United States Patent [19]
Hillan et al.

[11] Patent Number: 6,099,841
[45] Date of Patent: Aug. 8, 2000

[54] HEPATOCYTE GROWTH FACTOR RECEPTOR AGONISTS AND USES THEREOF

[75] Inventors: Kenneth J. Hillan, San Francisco; Ralph H. Schwall, Pacifica; Kelly H. Tabor, Hillsborough, all of Calif.

[73] Assignee: Genentech, Inc., South San Francisco, Calif.

[21] Appl. No.: 08/884,669

[22] Filed: Jun. 27, 1997

Related U.S. Application Data

[60] Provisional application No. 60/021,215, Jul. 3, 1996.

[51] Int. Cl.[7] .......................... C07K 16/28; C12N 15/06; A61K 39/395
[52] U.S. Cl. .................................... 424/143.1; 424/134.1; 424/135.1; 424/136.1; 424/138.1; 435/334; 530/387.7; 530/387.3; 530/388.22; 530/389.1; 530/389.2; 530/389.7; 530/350
[58] Field of Search .......................... 530/388.22, 389.1, 530/387.3, 350, 387.7, 389.7, 389.2; 435/334, 7.1; 514/2; 424/143.1, 134.1, 135.1, 136.1, 138.1

[56] References Cited

U.S. PATENT DOCUMENTS

| | | | |
|---|---|---|---|
| 4,342,566 | 8/1982 | Theofilopoulos et al. | 23/230 |
| 4,816,567 | 3/1989 | Cabilly et al. | 530/387 |
| 5,227,158 | 7/1993 | Jardieu | 424/85.5 |
| 5,316,921 | 5/1994 | Godowski et al. | 435/69.4 |
| 5,328,837 | 7/1994 | Godowski et al. | 435/69.4 |
| 5,648,273 | 7/1997 | Bottaro et al. | 435/501 |
| 5,686,292 | 11/1997 | Schwall et al. | 435/240.27 |

FOREIGN PATENT DOCUMENTS

| | | |
|---|---|---|
| 462549 A1 | 12/1991 | European Pat. Off. . |
| WO 92/13097 | 8/1992 | WIPO . |
| WO 92/20792 | 11/1992 | WIPO . |
| WO 93/15754 | 8/1993 | WIPO . |
| WO 93/16185 | 8/1993 | WIPO . |
| WO 93/25673 | 12/1993 | WIPO . |
| WO 94/04679 | 3/1994 | WIPO . |
| WO 94/06456 | 3/1994 | WIPO . |
| WO 94/29348 | 12/1994 | WIPO . |
| WO 95/07097 | 3/1995 | WIPO . |
| WO 96/40914 | 12/1996 | WIPO . |

OTHER PUBLICATIONS

*Handbook of Monoclonal Antibodies*, Ferrone et al. eds., Park Ridge, NJ:Noyes Publications, pp. 302–359 and Chapter 22 (1985).

Anderson, W.F., "Human gene therapy" *Science* 256:808–813 (1992).

Asami et al., "Purification and Characterization of Hepatocyte Growth Factor from Injured Liver of Carbon Tetrachloride–Treated Rats" *J. Biochem.* 109:8–13 (1991).

Bellusci et al., "Creation of an Hepatocyte Growth Factor/Scatter Factor Autocrine Loop in Carcinoma Cells Induces Invasive Properties Associated with Increased Tumorigenicity" *Oncogene* 9:1091–1099 (1994).

Boerner et al., "Production of Antigen–Specific Human Monoclonal Antibodies From In Vitro–Primed Human Splenocytes" *The Journal of Immunology* 147(1):86–95 (1991).

Bottaro et al., "Identification of the Hepatocyte Growth Factor Receptor as the c–met Proto–Oncogene Product" *Science* 251:801–804 (Feb. 15, 1991).

Brodeur et al., "Mouse–Human Myeloma Partners for the Production of Heterohybridomas" *Monoclonal Antibody Production Techniques and Applications*, New York:Marcel Dekker, Inc. pp. 51–63 (1987).

Bruggemann et al., "Designer Mice: The Production of Human Antibody Repertoires in Transgenic Animals" *Year in Immunology* 7:33–40 (1993).

Carter et al., "Humanization of an anti–p185$^{HER2}$ antibody for human cancer therapy" *Proc. Natl. Acad. Sci.* 89:4285–4289 (1992).

Chamow et al., "A Humanized, Bispecific Immunoadhesin–Antibody That Retargets $CD3^+$ Effectors to Kill HIV–1–Infected Cells" *Journal of Immunology* 153:4268–4280 (1994).

Chan et al., "Identification of a Competitive HGF Antagonist Encoded by an Alternative Transcript" *Science* 254:1382–1385 (1991).

Chan et al., "Isoforms of Human HGF and Their Biological Activities" *Hepatocyte Growth Factor–Scatter Factor (HGF–SF) and the C–Met Receptor*, I. D. Goldberg and E. M. Rosen eds., Basel:Birkhauser Verlag pp. 67–79 (1993).

Chothia and Lesk, "Canonical structures for the hypervariable regions of immunoglobulins" *J. Mol. Biol.* 196(4):901–917 (1987).

Chothia, Cyrus, "Domain Association in Immunoglobulin Molecules: The Packing of Variable Domains" *J. Mol. Biol.* 186:651–663 (1985).

Cole et al., "The EBV–Hybridoma Technique and Its Application to Human Lung Cancer" *Monoclonal Antibodies and Cancer Therapy*, Reisfeld et al., New York:Alan R. Liss, Inc. pp. 77–96 (1985).

Comoglio, "Structure, Biosynthesis and Biochemical Properties of the HGF Receptor in Normal and Malignant Cells" *Hepatocyte Growth Factor–Scatter Factor (HGF–SF) and the C–Met Receptor*, I. D. Goldberg and E. M. Rosen eds., Basel:Birkhauser Verlag pp. 131–165 (1993).

Cooper et al., "Amplification and Overexpression of the MET Gene in Spontaneously Transformed NIH3T3 Mouse Fibroblasts" *EMBO Journal* 5(10):2623–2628 (1986).

Copeland et al., "The Structure of Human Acidic Fibroblast Growth Factor and Its Interaction with Heparin" *Archives of Biochemistry & Biophysics* 289:53–61 (1991).

(List continued on next page.)

*Primary Examiner*—Lorraine Spector
*Assistant Examiner*—Claire M. Kaufman
*Attorney, Agent, or Firm*—Genentech, Inc.

[57] ABSTRACT

Hepatocyte growth factor (HGF) receptor agonists are provided. The HGF receptor agonists include HGF receptor antibodies and fragments thereof. The HGF receptor agonists can be employed to substantially enhance HGF receptor activation. The HGF receptor agonists may be included in pharmaceutical compositions, articles of manufacture, or kits. Methods of treatment and diagnosis using the HGF receptor agonists are also provided.

29 Claims, 9 Drawing Sheets

OTHER PUBLICATIONS

Crepaldi et al., "Targeting of the SF–HGF Receptor to the Basolateral Domain of Polarized Epithelial Cells" *The Journal of Cell Biology* 125(2):313–320 (1994).

Damon et al., "Heparin Potentiates the Action of Acidic Fibroblast Growth Factor by Prolonging Its Biological Half–Life" *J. Cellular Physiology* 138:221–226 (1989).

David et al., "Protein Iodination with Solid State Lactoperoxidase" *Biochemistry* 13(5):1014–1021 (1974).

de Sauvage et al., "Stimulation of Megakaryocytopoiesis and Thrombopoiesis by the c–Mpl Ligand" *Nature* 369:533–538 (Jun. 16, 1994).

Di Renzo et al., "Overexpression of the c–MET/HGF Receptor Gene in Human Thyroid Carcinomas" *Oncogene* 7:2549–2553 (1992).

Di Renzo et al., "Selective Expression of the Met/HGF Receptor in Human Central Nervous System Microglia" *Oncogene* 8:219–222 (1993).

Giordano et al., "Transfer of Motogenic and Invasive Response to Scatter Factor/Hepatocyte Growth Factor by Transfection of Human met Protooncogene" *Proc. Natl. Acad. Sci. USA* 90:649–653 (Jan. 1993).

Giordano et al., "Tyrosine Kinase Receptor Indistinguishable from the C–Met Protein" *Nature* 339:155–156 (May 11, 1989).

Goding, "Production of Monoclonal Antibodies" *Monoclonal Antibodies: Principles and Practice,* Academic Press, pp. 59–103 (1986).

Gohda et al., "Purification and Partial Characterization of Hepatocyte Growth Factor from Plasma of a Patient with Fulminant Hepatic Failure" *J. Clin. Invest.* 81:414–419 (1988).

Gorman, C., "High Efficiency Gene Transfer Into Mammalian Cells" *DNA Cloning: A Practical Approach,* Glover, D.M., ed, Washington D.C.:IRL Press vol. 2:143–190 (1985).

Han et al., "Characterization of the DNF15S2 Locus on Human Chromosomes 3: Identification of a Gene Coding for Four Kringle Domains with Homology to Hepatocyte Growth Factor" *Biochemistry* 30:9768–9780 (1991).

Hartmann et al., "A Functional Domain in the Heavy Chain of Scatter Factor/Hepatocyte Growth Factor Binds the c–Met Receptor and Induces Cell Dissociation but Not Mitogenesis" *Proc. Natl. Acad. Sci. USA* 89:11574–11578 (Dec. 1992).

Hoogenboom and Winter, "By–passing immunisation: human antibodies from synthetic repertoires of germline $V_H$ gene segments rearranged in vitro" *J. Mol. Biol.* 227:381–388 (1992).

Hunter et al., "Preparation of Iodine 131 Labelled Human Growth Hormone of High Specific Activity" *Nature* 194:495–496 (1962).

Igawa et al., "Hepatocyte Growth Factor is a Potent Mitogen for Cultured Rabbit Renal Tubular Epithelial Cells" *Biochem & Biophys. Res. Comm.* 174(2):831–838 (Jan. 31, 1991).

Iyer et al., "Structure, Tissue–Specific Expression, and Transforming Activity of the Mouse met Protooncogene" *Cell Growth & Differentiation* pp. 87–95 (1990).

Jakobovits et al., "Analysis of Homozygous Mutant Chimeric Mice: Deletion of the Immunoglobulin Heavy–Chain Joining Region Blocks B–cell Development and Antibody Production" *Proc. Natl. Acad. Sci. USA* 90:2551–2555 (1993).

Jakobovits et al., "Germ–line Transmission and Expression of a Human–Derived Yeast Artificial Chromosome" *Nature* 362:255–258 (1993).

Jones et al., "Replacing the Complementarity–determining Regions in a Human Antibody with Those From a Mouse" *Nature* 321:522–525 (May 29, 1986).

Kohler and Milstein, "Continuous cultures of fused cells secreting antibody of predefined specificity" *Nature* 256:495–497 (1975).

Kozbor et al., "A Human Hybrid Myeloma for Production of Human Monoclonal Antibodies" *The Journal of Immunology* 133(6):3001–3005 (1984).

Krasnoselsky et al., "Hepatocyte Growth Factor Is a Mitogen for Schwann Cells and Is Present in Neurofibromas" *J. Neuroscience* 14:7284–7290 (1994).

Lindahl et al., "Glycosaminoglycans and Their Binding to Biological Macromolecules" *Annual Rev. Biochem.* 47:385–417 (1978).

Lindroos et al., "Hepatocyte Growth Factor (Hepatopoietin A) Rapidly Increases in Plasma before DNA Synthesis and Liver Regeneration Stimulated by Partial Hepatectomy and Carbon Tetrachloride Administration" *Hepatology* 13(4):743–750 (1991).

Lokker et al., "Generation and Characterization of a Competitive Antagonist of Human Hepatocyte Growth Factor, HGF/NK1" *Journal of Biological Chemistry* 268(23):17145–17150 (Aug. 15, 1993).

Lokker et al., "Structure–Function Analysis of Hepatocyte Growth Factor: Identification of Variants that Lack Mitogenic Activity Yet Retain High Affinity Receptor Binding" *EMBO Journal* 11(7):2503–2510 (1992).

Lyon et al., "Interaction of Hepatocyte Growth Factor with Heparin Sulfate" *Journal of Biological Chemistry* 269:11216–11223 (1994).

Mark et al., "Expression and Characterization of Hepatocyte Growth Factor Receptor–IgG Fusion Proteins" *The Journal of Biological Chemistry* 267(36):26166–26171 (Dec. 25, 1992).

Marks et al., "By–passing immunization: human antibodies from V–gene libraries displayed on phage" *J. Mol. Biol.* 222:581–597 (1991).

Matsumoto et al., "Deletion of Kringle Domains or the N–Terminal Hairpin Structure in Hepatocyte Growth Factor Results in Marked Decreases in Related Biological Activities" *Biochem. & Biophys. Res. Comm.* 181(2):691–699 (Dec. 16, 1991).

Matsumoto et al., "Hepatocyte Growth Factor is a Potent Stimulator of Human Melanocyte DNA Synthesis and Growth" *Biochem. & Biophys. Res. Comm.* 176(1):45–51 (Apr. 15, 1991).

Michalopoulos et al., "Control of Hepatocyte Replication by Two Serum Factors" *Cancer Research* 44:4414–4419 (Oct. 1984).

Miyazawa et al., "An Alternatively Processed mRNA Generated from Human Hepatocyte Growth Factor Gene" *European Journal of Biochemistry* 197:15–22 (1991).

Miyazawa et al., "Molecular Cloning and Sequence Analysis of cDNA for Human Hepatocyte Growth Factor" *Biochem. & Biophys. Res. Comm.* 163(2):967–973 (Sep. 15, 1989).

Mizuno et al., "Hairpin loop and second kringle domain are essential sites for heparin binding and biological activity of hepatocyte growth factor" *Journal of Biological Chemistry* 269(2):1131–1136 (1994).

Montesano et al., "Identification of a Fibroblast–Derived Epithelial Morphogen as Hepatocyte Growth Factor" *Cell* 67:901–908 (Nov. 29, 1991).

Morrison et al., "Chimeric Human Antibody Molecules: Mouse Antigen–binding Domains with Human Constant Region Domains" *Proc. Natl. Acad. Sci. USA* 81:6851–6855 (Nov. 1984).

Moscatelli et al., "Basic Fibroblast Growth Factor (bFGF) Dissociates Rapidly from Heparan Sulfates but Slowly from Receptors" *Journal of Biological Chemistry* 267:25803–25809 (1992).

Mueller et al., "Stabilization by Heparin of Acidic Fibroblast Growth Factor Mitogenicity for Human Endothelial Cells in Vitro" *J. Cell. Phys.* 140:439–448 (1989).

Munson et al., "Ligand: A Versatile Computerized Approach for Characterization of Ligand–Binding Systems" *Analytical Biochemistry* 107:220–239 (1980).

Naka et al., "Activation of Hepatocyte Growth Factor by Proteolytic Conversion of a Single Chain Form to a Heterodimer" *The Journal of Biological Chemistry* 267(28):20114–20119 (1992).

Nakumura et al., "Molecular Cloning and Expression of Human Hepatocyte Growth Factor" *Nature* 342:440–443 (Nov. 23, 1989).

Nakamura et al., "Partial Purification and Characterization of Hepatocyte Growth Factor from Serum of Hepatectomized Rats" *Biochem. & Biophys. Res. Comm.* 122:1450–1459 (Aug. 16, 1984).

Nakamura et al., "Purification and Characterization of a Growth Factor from Rat Platelets for Mature Parenchymal Hepatocytes in Primary Cultures," *Proc. Natl. Acad. Sci. USA* 83:6489–6493 (1986).

Nakamura et al., "Purification and Subunit Structure of Hepatocyte Growth Factor from Rat Platelets" *FEBS Letters* 224(2):311–316 (Nov. 1987).

Naldini et al., "Hepatocyte Growth Factor (HGF) Stimulates the Tyrosine Kinase Activity of the Receptor Encoded by the Proto–Oncogene c–MET" *Oncogene* 6:501–504 (1991).

Naldini et al., "Scatter Factor and Hepatocyte Growth Factor are Indistinguishable Ligands for the MET Receptor" *EMBO Journal* 10(10):2867–2878 (1991).

Novotny and Haber, "Structural invariants of antigen binding: comparison of Immunoglobulin $V_L$–$V_H$ and $V_L$–$V_l$ domain dimers" *Proc. Natl. Acad. Sci. USA* 82(14):4592–4596 (Jul 1985).

Nugent et al., "Kinetics of Basic Fibroblast Growth Factor Binding to Its Receptor and Heparan Sulfate Proteoglycan: A Mechanism for Cooperativity" *Biochemistry* 31:8876–8883 (1992).

Nygren, "Conjugation of Horseradish Peroxidase to Fab Fragments with Different Homobifunctional and Heterobifunctional Cross–Linking Reagents" *The Journal of Histochemistry and Cytochemistry* 30(5):407–412 (1982).

Okajima et al., "Primary Structure of Rat Hepatocyte Growth Factor and Induction of Its mRNA During Liver Regeneration Following Hepatic Injury" *European Journal of Biochemistry* 193:375–381 (1990).

Ornitz et al., "Heparin Is Required for Cell–Free Binding of Basic Fibroblast Growth Factor to a Soluble Receptor and for Mitogenesis in Whole Cells" *Molecular & Cellular Biology* 12:240–247 (1992).

Pain et al., "Preparation of Protein A–Peroxidase Monoconjugate Using a Heterobifunctional Reagent, and its Use in Enzyme Immunoassays" *Journal of Immunological Methods* 40:219–230 (1981).

Palacios et al., "IL3–Dependent Mouse Clones That Express B–220 Surface Antigen, Contain Ig Genes in Germ–Line Configuration, and Generate B Lymphocyte In Vivo" *Cell* 41:727–734 (1985).

Park et al., "Sequence of MET Protooncogene cDNA has Features Characteristic of the Tyrosine Kinase Family of Growth–Factor Receptors" *Proc. Natl. Acad. Sci. USA* 84:6379–6383 (1987).

Ponzetto et al., "c–met is Amplified But Not Mutated in a Cell Line with an Activated met Tyrosine Kinase" *Oncogene* 6:553–559 (1991).

Prat et al., "C–Terminal Truncated Forms of Met, the Hepatocyte Growth Factor Receptor" *Molecular & Cellular Biology* 11(12):5954–5962 (1991).

Prat et al., "The Receptor Encoded by the Human c–Met Oncogene is Expressed in Hepatocytes, Epithelial Cells and Solid Tumors" *Int. J. Cancer* 49:323–328 (1991).

Presta, "Antibody engineering" *Curr. Op. Struct. Biol.* 2:593–596 (1992).

Presta et al., "Humanization of an Antibody Directed Against IgE" *J. Immunol.* 151(5):2623–2632 (Sep. 1, 1993).

Riechman et al., "Reshaping human antibodies for therapy" *Nature* 332:323–327 (1988).

Rodrigues et al., "Alternative Splicing Generates Isoforms of the met Receptor Tyrosine Kinase Which Undergo Differential Processing" *Molecular & Cellular Biology* 11(6):2962–2970 (1991).

Rosengart et al., "Heparin Protects Heparin–Binding Growth Factor–I From Proteolytic Inactivation In Vitro" *Biochem. & Biophys. Res. Comm.* 152:432–440 (1988).

Rubin et al., "A Broad–Spectrum Human Lung Fibroblast–Derived Mitogen is a Variant of Hepatocyte Growth Factor" *Proc. Natl. Acad Sci. USA* 88:415–419 (1991).

Ruoslahti et al., "Proteoglycans as Modulators of Growth Factor Activities" *Cell* 64(5):867–869 (1991).

Russell et al., "Partial Characterization of a Hepatocyte Growth Factor From Rat Platelets" *J. Cellular Physiology* 119:183–192 (1984).

Sadick et al., "Analysis of Heregulin–Induced ErbB2 Phosphorylation with a High–Throughput Kinase Receptor Activation Enzyme–Linked Immounosorbent Assay" *Analytical Biochemistry* 235:207–214 (1996).

Seglen, "Preparations of Isolated Rat Liver Cells" *Meth. Cell. Biol.,* Chapter 4, 13:29–83 (1976).

Seki et al., "Isolation and Expression of cDNA for Different Forms of Hepatocyte Growth Factor from Human Leukocyte" *Biochem. and Biophys. Res. Commun.* 172(1):321–327 (Oct. 15, 1990).

Silvagno et al., "In Vivo Activation of Met Tyrosine Kinase by Heterodimeric Hepatocyte Growth Factor Molecule Promotes Angiogenesis" *Arterioscler. Thromb. Vasc. Biol.* 15:1857–1865 (1995).

Sims et al., "A Humanized CD18 Antibody Can Block Function Without Cell Destruction" *The Journal of Immunology* 151(4):2296–2308 (1993).

Smith et al., "Cardiac Glycoside–Specific Antibodies in the Treatment of Digitalis Intoxication" *Antibodies in Human Diagnosis and Therapy* pp. 365–389 (1977).

Spivak–Kroizman et al., "Heparin–Induced Oligomerization of FGF Molecules Is Responsible for FGF Receptor Dimerization, Activation and Cell Proliferation" *Cell* 79:1015–1024 (1994).

Stoker et al., "Scatter Factor is a Fibroblast–Derived Modulator of Epithelial Cell Mobility" *Nature* 327:239–242 (May 21, 1987).

Tashiro et al., "Deduced Primary Structure of Rat Hepatocyte Growth Factor and Expression of the mRNA in Rat Tissues" *Proc. Natl. Acad. Sci. USA* 87:3200–3204 (1990).

Upstate Biotechnology Inc. Anti–human Met Monoclonal Antibodies (product literature).

Verhoeyen et al., "Reshaping Human Antibodies: Grafting an Antilysozyme Activity" *Science* 239:1534–1536 (Mar. 25, 1988).

Wagner, J., "Linear pharmacokinetic equations allowing direct calculation of many needed pharmacokinetic parameters from the coefficients and exponents of polyexponential equations which have been fitted to the data" *J. Pharmacokinetics and Biopharmaceutics* 4(5):443–467 (1976).

Weidner et al., "Scatter Factor: Molecular Characteristics and Effect on the Invasiveness of Epithelial Cells" *Journal of Cell Biology* 111:2097–2108 (Nov. 1990).

Yamada et al., "Immunohistochemistry with Antibodies to Hepatocyte Growth Factor and Its Receptor Protein (c–MET) in Human Brain Tissues" *Brain Research* 637:308–312 (1994).

Yayon et al., "Cell Surface, Heparin–like Molecules Are Required for Binding of Basic Fibroblast Growth Factor to its High Affinity Receptor" *Cell* 64:841–848 (1991).

Zioncheck et al., "Sulfated Oligosaccharides Promote Hepatocyte Growth Factor Association and Govern Its Mitogenic Activity" *Journal of Biological Chemistry* 270:16871–16878 (1995).

Zola, "Using Monoclonal Antibodies: Soluble Antigens" *Monoclonal Antibodies: A Manual of Techniques,* CRC Press, Chapter 6, pp. 147–158 (1987).

Chang et al., "Agonistic Antibodies to c–MET, The HGF Receptor, Selectively Stimulate Proliferation vs. Migration" *FASEB J.* (abstract only) 11(3):A523 (1997).

Galimi et al., "Hepatocyte Growth Factor Induces Proliferation and Differentiation of Multipotent and Erythroid Hemopoietic Progenitors" *Journal of Cell Biology* 127(6):1743–1754 (1994).

Hillan et al., "Stimulation of Hepatocyte Proliferation and Liver Growth in Ferrets by an Agonistic Antibody to the c–MET Receptor" *J. Path.* (abstract only) 179:33A (1996).

Prat et al., "The HGF Receptor (Met): Transduction of Signals for Invasive Cell Growth" *Antibody, Immunoconjugates, and Radiopharmaceuticals* 8(4):341–361 (1995).

Tabor et al., "Monoclonal Antibodies to the Human c–MET/HGF Receptor Act as Agonists" The 9th International Congress on Immunology (abstract only) pp. 870 (Jul. 1995).

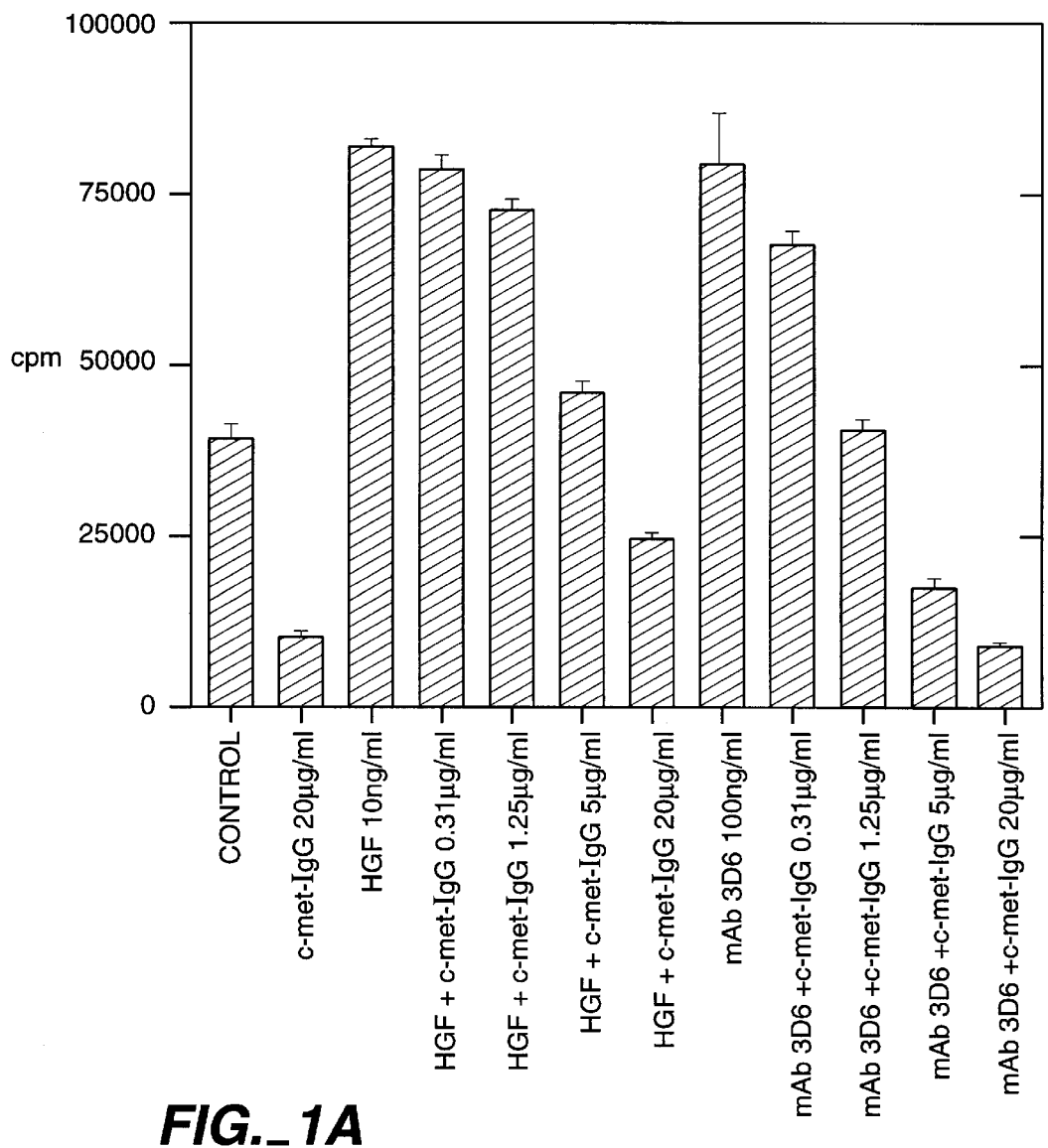
FIG._1A

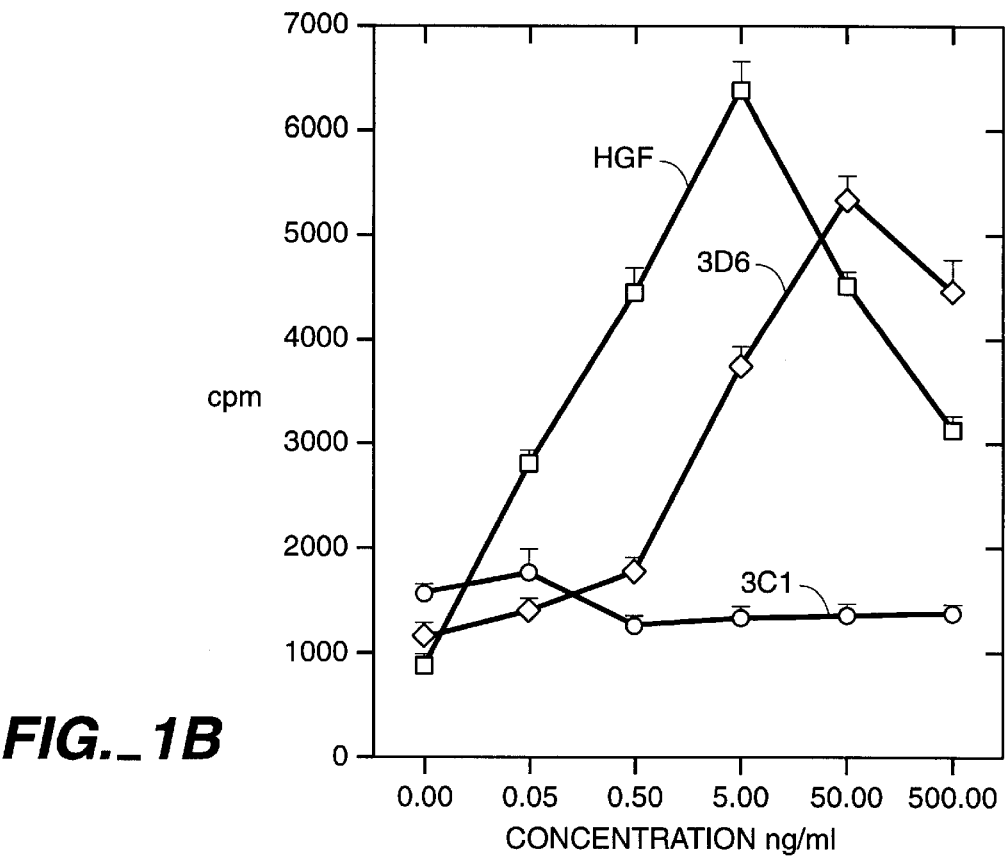
FIG._1B
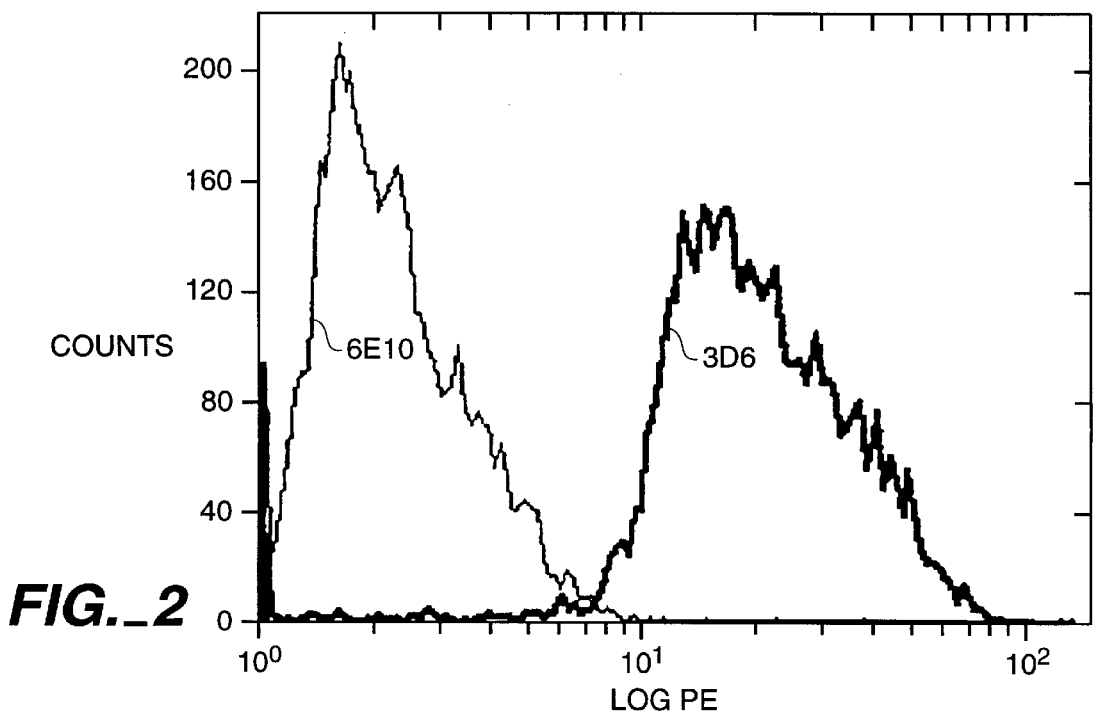
FIG._2

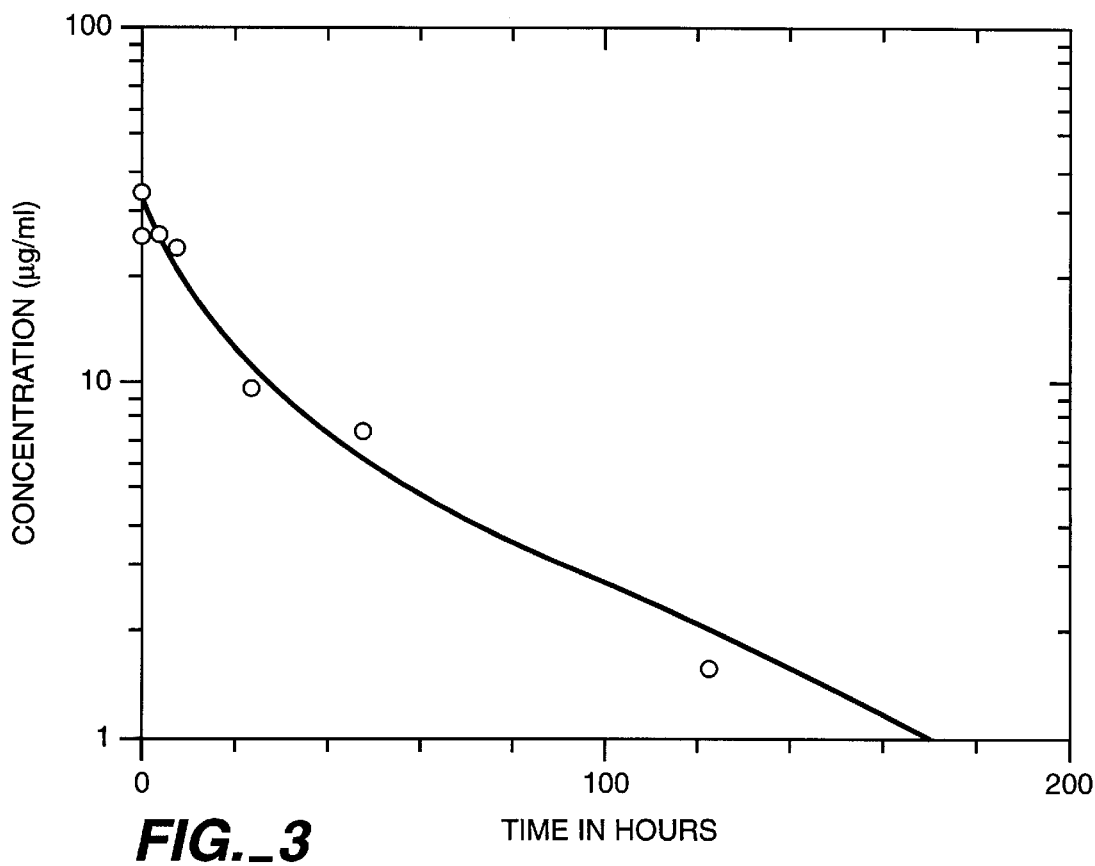
FIG._3
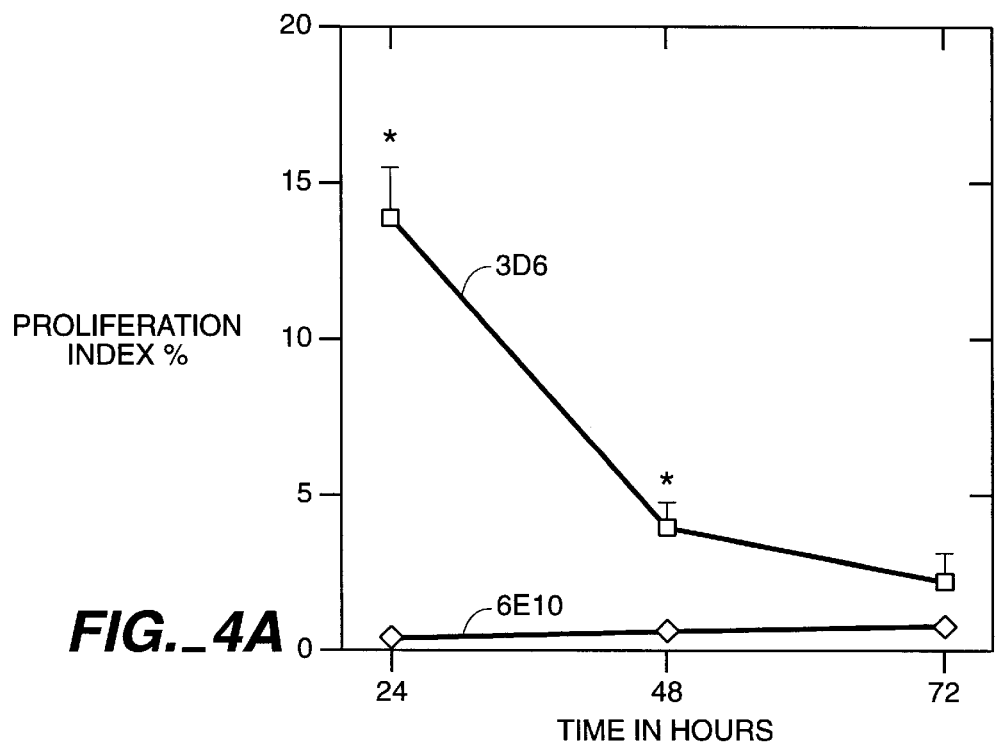
FIG._4A

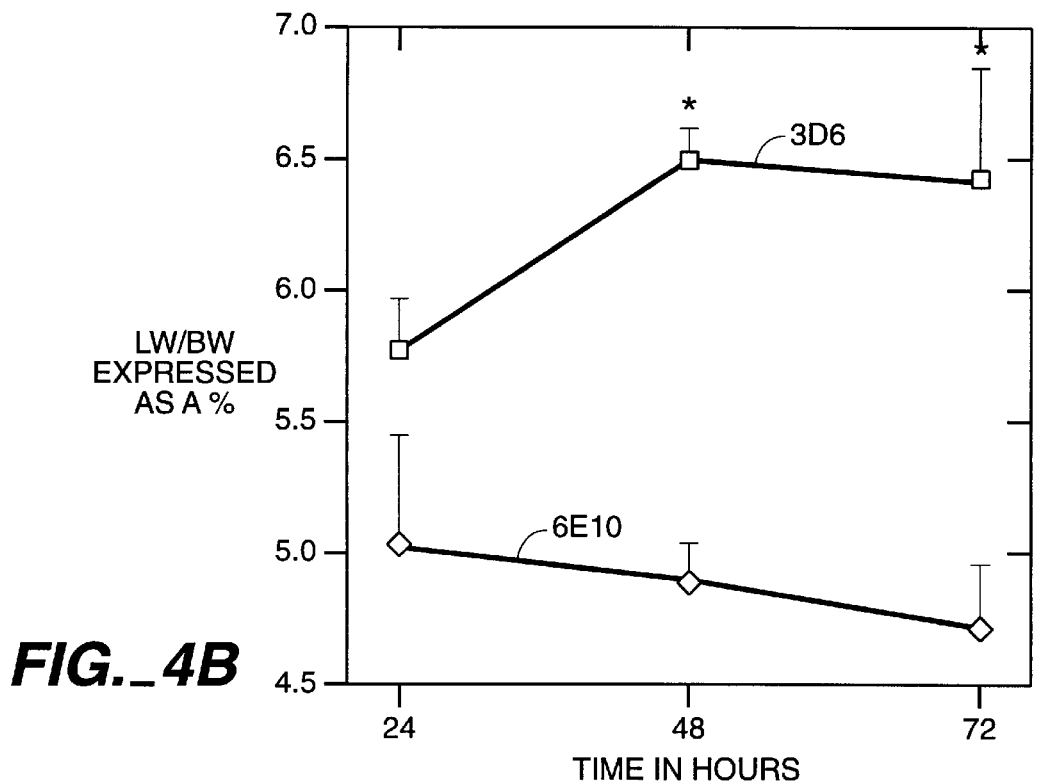
FIG._4B
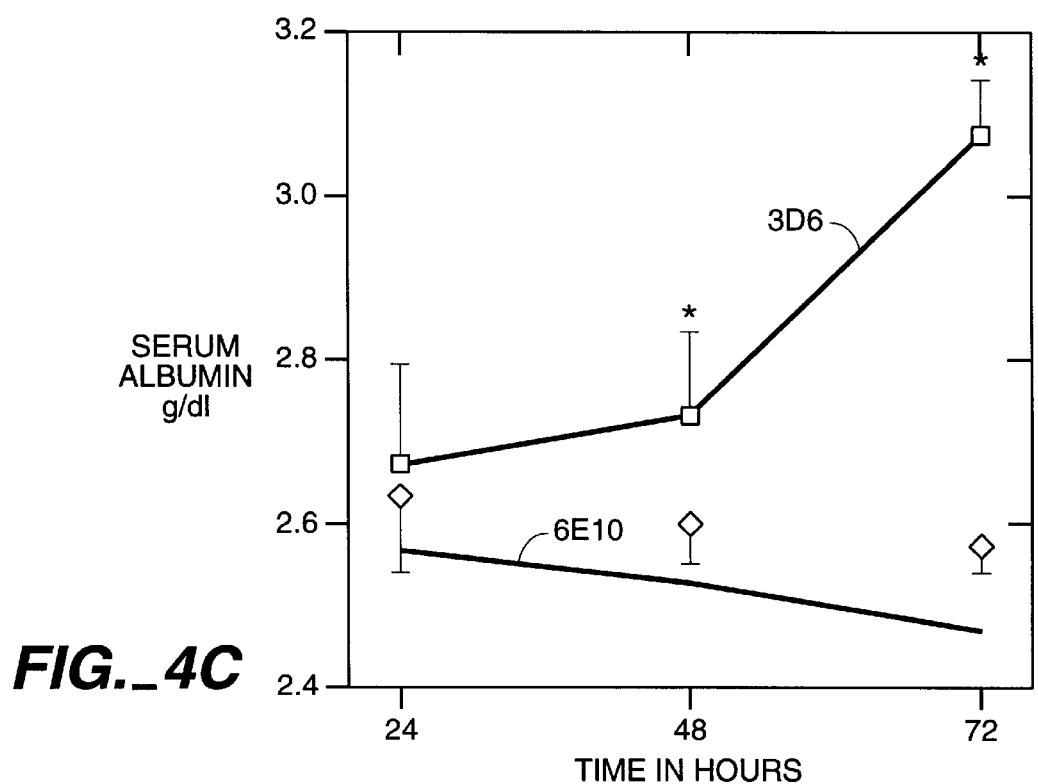
FIG._4C

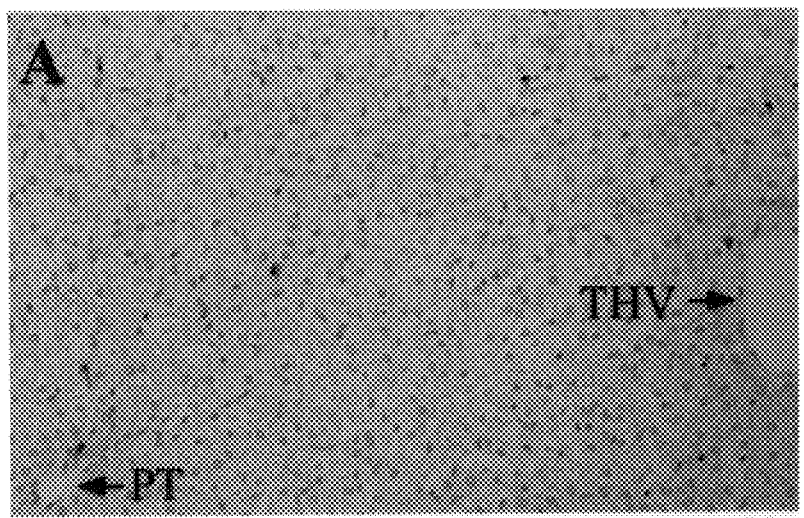
FIG._5A
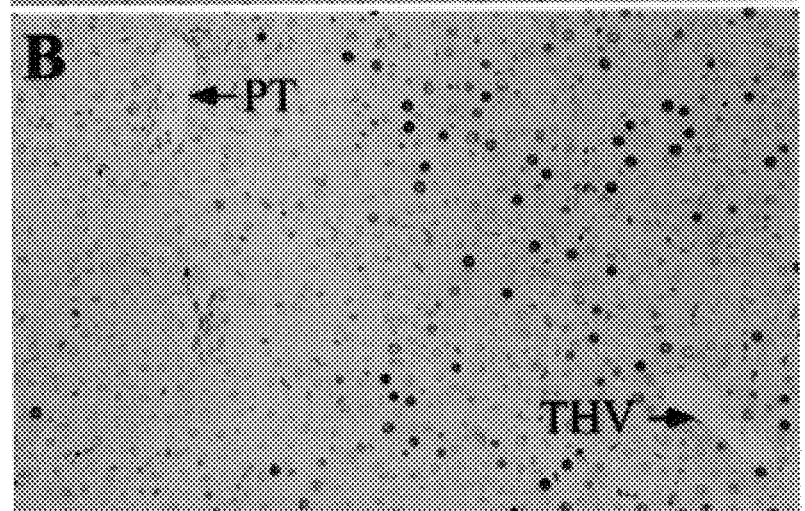
FIG._5B
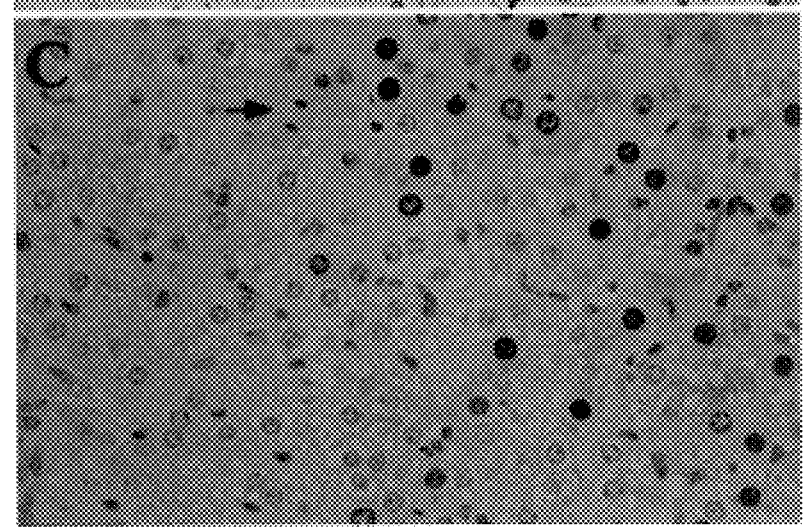
FIG._5C

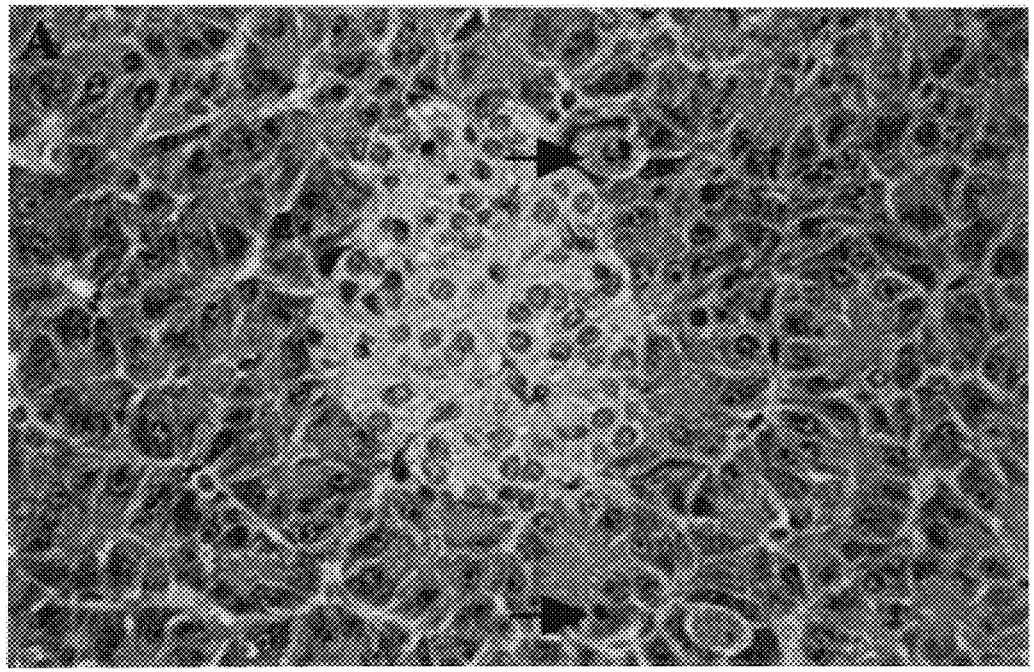
FIG._6A
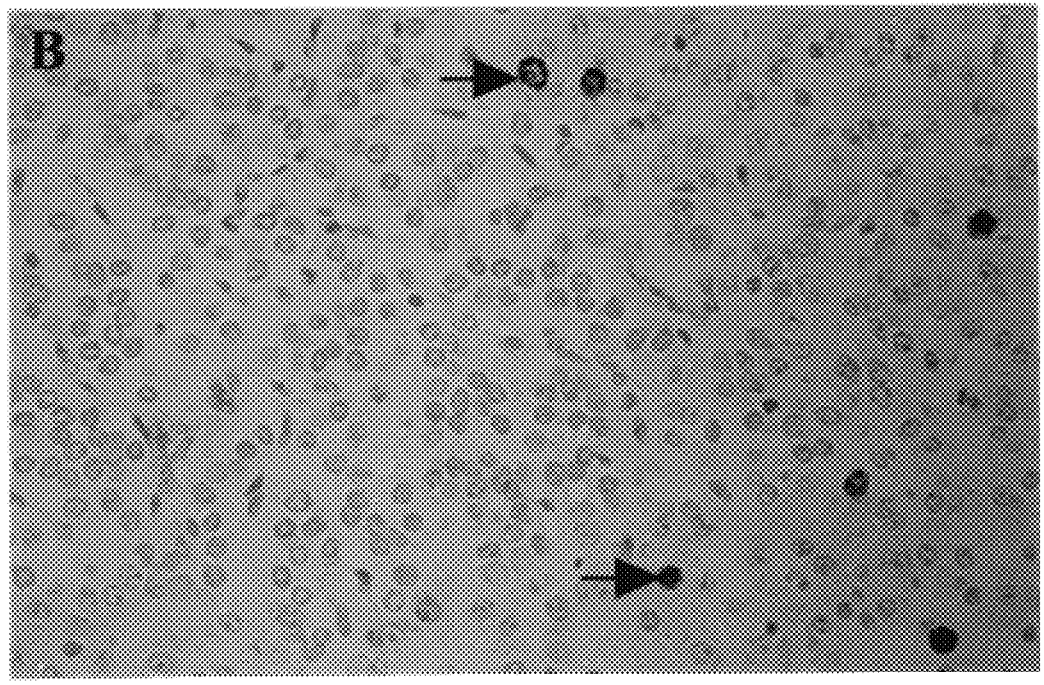
FIG._6B

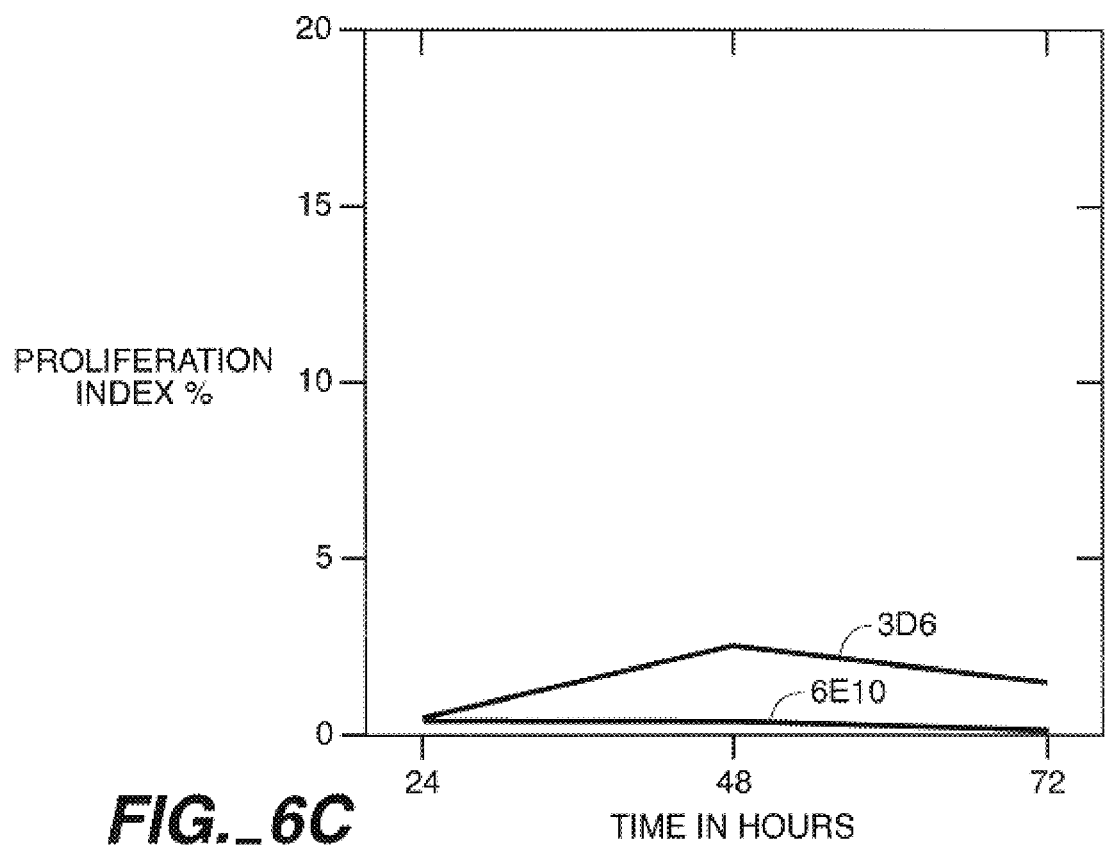
FIG._6C
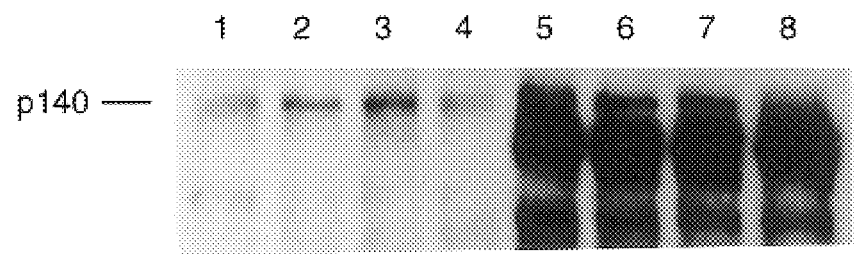
FIG._8

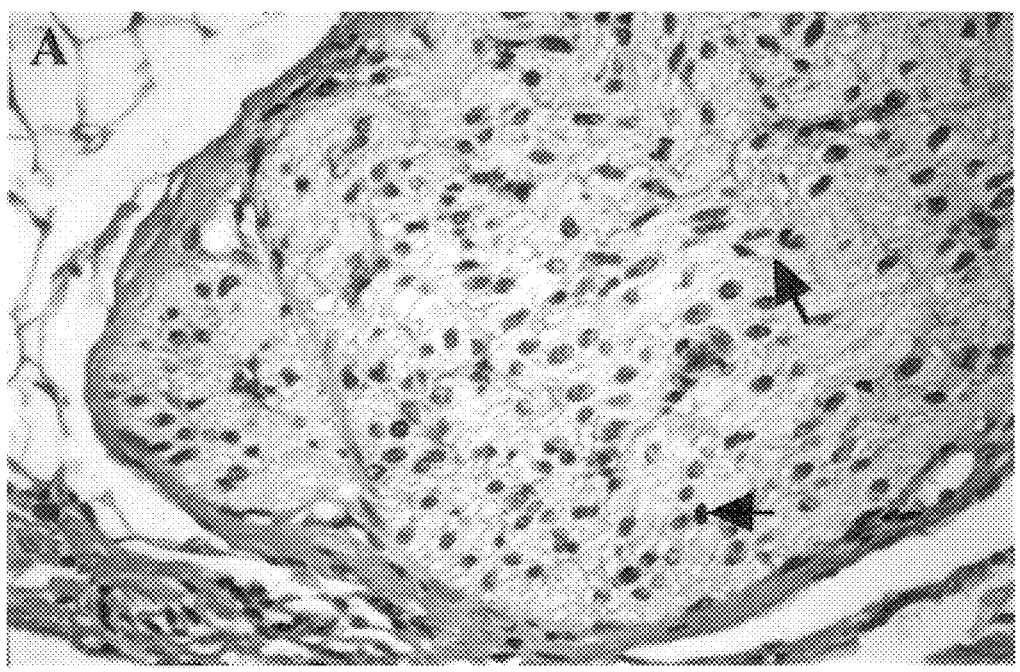
FIG._7A
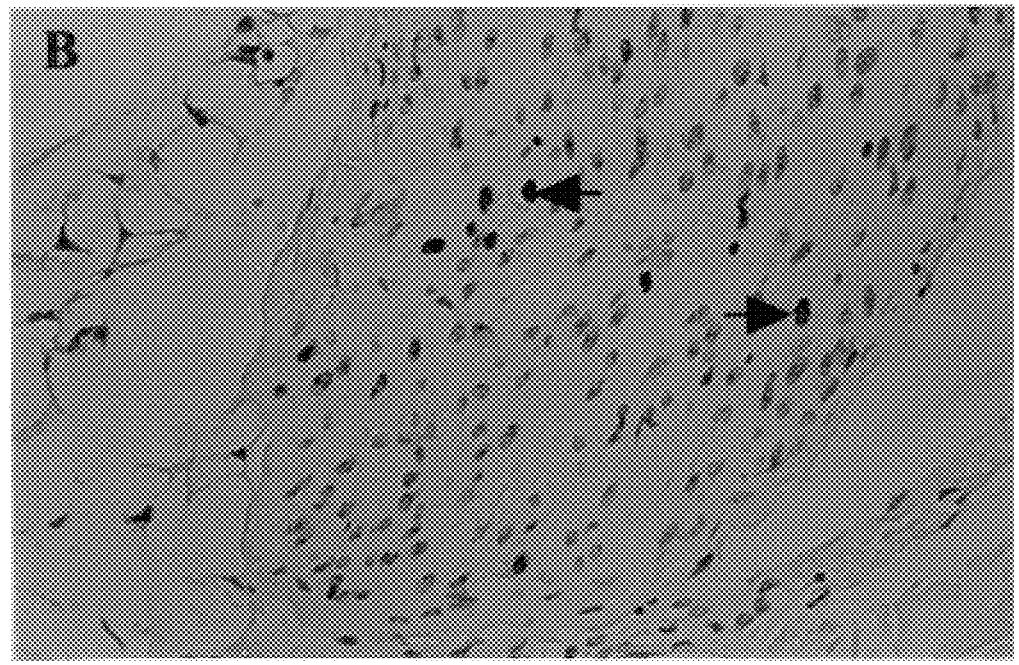
FIG._7B

| STIMULANT | CONCENTRATION | P-Tyr-c-Met (AU) | TOTAL c-Met (AU) |
|---|---|---|---|
| CONTROL | | 0.058 ± 0.002 | 0.752 ± 0.005 |
| HGF | 100 ng/ml | 0.541 ± 0.037 | 0.661 ± 0.025 |
| ANTI-c-Met 3D6 | 1μg/ml | 0.645 ± 0.004 | 0.740 ± 0.013 |
| | 10μg/ml | 0.862 ± 0.014 | 0.717 ± 0.016 |
| ANTI-gp120 6E10 | 1μg/ml | 0.070 ± 0.001 | 0.846 ± 0.004 |
| | 10μg/ml | 0.070 ± 0.011 | 0.833 ± 0.071 |

FIG._9

HEPATOCYTE GROWTH FACTOR RECEPTOR AGONISTS AND USES THEREOF

RELATED APPLICATIONS

This application is a non-provisional application filed under 37 CFR 1.53(b)(1) claiming priority under 35 USC 119(e) to provisional application Ser. No. 60/021,215 filed Jul. 3, 1996, the contents of which are incorporated herein by reference.

FIELD OF THE INVENTION

This application relates to hepatocyte growth factor receptor agonists, including agonistic antibodies. The application also relates to the use of the agonists in therapy or diagnosis of particular pathological conditions in mammals.

BACKGROUND OF THE INVENTION

Hepatocyte growth factor ("HGF") functions as a growth factor for particular tissues and cell types. HGF was identified initially as a mitogen for hepatocytes [Michalopoulos et al., Cancer Res., 44:4414–4419 (1984); Russel et al., J. Cell. Physiol., 119:183–192 (1984); Nakamura et al., Biochem. Biophys. Res. Comm., 122:1450–1459 (1984)]. Nakamura et al., supra, reported the purification of HGF from the serum of partially hepatectomized rats. Subsequently, HGF was purified from rat platelets, and its subunit structure was determined [Nakamura et al., Proc. Natl. Acad. Sci. USA, 83:6489–6493 (1986); Nakamura et al., FEBS Letters, 224:311–316 (1987)]. The purification of human HGF ("huHGF") from human plasma was first described by Gohda et al., J. Clin. Invest., 81:414–419 (1988).

Both rat HGF and huHGF have been molecularly cloned, including the cloning and sequencing of a naturally occurring variant lacking 5 amino acids designated "delta5 HGF" [Miyazawa et al., Biochem. Biophys. Res. Comm., 163:967–973 (1989); Nakamura et al., Nature, 342:440–443 (1989); Seki et al., Biochem. Biophys. Res. Commun., 172:321–327 (1990); Tashiro et al., Proc. Natl. Acad. Sci. USA, 87:3200–3204 (1990); Okajima et al., Eur. J. Biochem., 193:375–381 (1990)].

The mature form of huHGF, corresponding to the major form purified from human serum, is a disulfide linked heterodimer derived by proteolytic cleavage of the human pro-hormone between amino acids R494 and V495. This cleavage process generates a molecule composed of an α-subunit of 440 amino acids ($M_r$ 69 kDa) and a β-subunit of 234 amino acids ($M_r$ 34 kDa). The nucleotide sequence of the huHGF cDNA reveals that both the α- and the β-chains are contained in a single open reading frame coding for a pre-pro precursor protein. In the predicted primary structure of mature huHGF, an interchain S-S bridge is formed between Cys 487 of the α-chain and Cys 604 in the β-chain [see Nakamura et al., Nature, supra]. The N-terminus of the α-chain is preceded by 54 amino acids, starting with a methionine group. This segment includes a characteristic hydrophobic leader (signal) sequence of 31 residues and the prosequence. The α-chain starts at amino acid (aa) 55, and contains four kringle domains. The kringle 1 domain extends from about aa 128 to about aa 206, the kringle 2 domain is between about aa 211 and about aa 288, the kringle 3 domain is defined as extending from about aa 303 to about aa 383, and the kringle 4 domain extends from about aa 391 to about aa 464 of the α-chain.

The definition of the various kringle domains is based on their homology with kringle-like domains of other proteins (such as prothrombin and plasminogen), therefore, the above limits are only approximate. To date, the function of these kringles has not been determined. The β-chain of huHGF shows high homology to the catalytic domain of serine proteases (38% homology to the plasminogen serine protease domain). However, two of the three residues which form the catalytic triad of serine proteases are not conserved in huHGF. Therefore, despite its serine protease-like domain, huHGF appears to have no proteolytic activity, and the precise role of the β-chain remains unknown. HGF contains four putative glycosylation sites, which are located at positions 294 and 402 of the α-chain and at positions 566 and 653 of the β-chain.

Comparisons of the amino acid sequence of rat HGF with that of huHGF have revealed that the two sequences are highly conserved and have the same characteristic structural features. The length of the four kringle domains in rat HGF is exactly the same as in huHGF. Furthermore, the cysteine residues are located in exactly the same positions, an indication of similar three-dimensional structures [Okajima et al., supra; Tashiro et al., supra].

In a portion of cDNA isolated from human leukocytes, in-frame deletion of 15 base pairs was observed. Transient expression of the cDNA sequence in COS-1 cells revealed that the encoded HGF molecule (delta5 HGF) lacking 5 amino acids in the kringle 1 domain was fully functional [Seki et al., supra].

A naturally occurring huHGF variant has been identified which corresponds to an alternative spliced form of the huHGF transcript containing the coding sequences for the N-terminal finger and first two kringle domains of mature huHGF [Chan et al., Science, 254:1382–1385 (1991); Miyazawa et al., Eur. J. Biochem., 197:15–22 (1991)]. This variant, designated HGF/NK2, has been proposed by some investigators to be a competitive antagonist of mature huHGF. Hartmann et al. have reported, however, that HGF/NK2 may retain the ability to cause MDCK cells to scatter [Hartmann et al., Proc. Natl. Acad. Sci., 89:11574–11578 (1992)].

Another HGF variant, designated HGF/NK1, has also been reported to act as a competitive antagonist of HGF [Lokker et al., J. Biol. Chem., 268:17145–17150 (1993); Lokker et al., EMBO J., 11:2503–2510 (1992)]. That HGF/NK1 molecule, containing the N-terminal hairpin and the first kringle domain, was found to block binding of HGF to the HGF receptor on A549 human lung carcinoma cells. It was also found, however, that certain concentrations of the HGF/NK1 induced a detectable increase in receptor tyrosine phosphorylation in the A549 cells, suggesting some agonistic activity. Accordingly, it is believed that the agonist or antagonist action of HGF/NK1 may be dependent upon cell type.

HGF and HGF variants are described further in U.S. Pat. Nos. 5,227,158, 5,316,921, and 5,328,837.

A high affinity receptor for HGF has been identified as the product of the c-Met proto-oncogene [Bottaro et al., Science, 251:802–804 (1991); Naldini et al., Oncogene, 6:501–504 (1991); WO 92/13097 published Aug. 6, 1992; WO 93/15754 published Aug. 19, 1993]. This receptor is usually referred to as "c-Met" or "p190$^{MET}$" and typically comprises, in its native form, a 190-kDa heterodimeric (a disulfide-linked 50-kDa α-chain and a 145-kDa β-chain) membrane-spanning tyrosine kinase protein [Park et al., Proc. Natl. Acad. Sci. USA, 84:6379–6383 (1987)]. Several truncated forms of the c-Met receptor have also been described [WO 92/20792; Prat et al., Mol. Cell. Biol., 11:5954–5962 (1991)].

The binding activity of HGF to c-Met is believed to be conveyed by a functional domain located in the N-terminal portion of the HGF molecule, including the first two kringles [Matsumoto et al., *Biochem. Biophys. Res. Commun.*, 181:691–699 (1991); Hartmann et al., *Proc. Natl. Acad. Sci.*, 89:11574–11578 (1992); Lokker et al., *EMBO J.*, 11:2503–2510 (1992); Lokker and Godowski, *J. Biol. Chem.*, 268:17145–17150 (1991)]. The c-Met protein becomes phosphorylated on tyrosine residues of the 145-kDa β-subunit upon HGF binding.

Certain antibodies to this HGF receptor have been reported in the literature. Several such antibodies are described below.

Prat et al., *Mol. Cell. Biol.*, supra, describe several monoclonal antibodies specific for the extracellular domain of the β-chain encoded by the c-Met gene [see also, WO 92/20792]. The monoclonal antibodies were selected following immunization of Balb/c mice with whole living GTL-16 cells (human gastric carcinoma cell line) overexpressing the Met protein. The spleen cells obtained from the immunized mice were fused with Ag8.653 myeloma cells, and hybrid supernatants were screened for binding to GTL-16 cells. Four monoclonal antibodies, referred to as DL-21, DN-30, DN-31 and DO-24, were selected.

Prat et al., *Int. J. Cancer*, 49:323–328 (1991) describe using anti-c-Met monoclonal antibody DO-24 for detecting distribution of the c-Met protein in human normal and neoplastic tissues [see, also, Yamada et al., *Brain Research*, 637:308–312 (1994)]. The murine monoclonal antibody DO-24 was reported to be an IgG2a isotype antibody.

Crepaldi et al., *J. Cell Biol.*, 125: 313–320 (1994) report using monoclonal antibodies DO-24 and DN-30 [described in Prat et al., *Mol. Cell. Biol.*, supra] and monoclonal antibody DQ-13 to identify subcellular distribution of HGF receptors in epithelial tissues and in MDCK cell monolayers. According to Crepaldi et al., monoclonal antibody DQ-13 was raised against a peptide corresponding to nineteen COOH-terminal amino acids (from $Ser^{1372}$ to $Ser^{1390}$) of the human c-Met sequence.

A monoclonal antibody specific for the cytoplasmic domain of human c-Met has also been described [Bottaro et al., supra].

Silvagno et al., *Arterioscler. Throm. Vasc. Biol.*, 15:1857–1865 (1995) describe using a c-Met agonistic antibody in vivo to promote eangiogenesis in Matrigel plugs.

Several of the monoclonal antibodies referenced above are commercially available from Upstate Biotechnology Incorporated, Lake Placid, N.Y. Monoclonal antibodies DO-24 and DL-21, specific for the extracellular epitope of c-Met, are available from Upstate Biotechnology Incorporated. Monoclonal antibody DQ-13, specific for the intracellular epitope of c-Met, is also available from Upstate Biotechnology Incorporated.

In addition to binding c-Met, it is recognized that HGF binds to some heparin and heparan sulfate proteoglycans which are present on cell surfaces or in extracellular matrices [Ruoslahti et al., *Cell*, 64:867–869 (1991); Lyon et al., *J. Biol. Chem.*, 269:11216–11223 (1994)]. Heparan sulfate is a glycosaminoglycan similar in composition and structure to heparin and is found on many mammalian cell surfaces. Various hypotheses have been proposed to explain the role of heparin and heparan sulfate proteoglycans ("HPSGs") in the regulation of certain growth factor activity. For example, it has been hypothesized that upon binding heparin or HSPGs, certain growth factors may have a more favorable conformation for binding to their respective high affinity receptors [Lindahl et al., *Annual Rev. Biochem.*, 47:385–417 (1995)]; that HSPGs may serve as docking sites for certain growth factors facilitating the presentation of ligand to its high affinity receptor [Yayon et al., *Cell*, 64:841–848 (1991); Moscatelli et al., *J. Biol. Chem.*, 267:25803–25809 (1992); Nugent et al., *Biochemistry*, 31:8876–8883 (1992)]; and that HSPGs may promote ligand dimerization facilitating receptor activation [Ornitz et al., *Mol. Cell. Biol.*, 12:240–247 (1992); Spivak-Kroizman et al., *Cell*, 79:1015–1024 (1994)]. It has further been postulated that certain growth factors are more stable or resistant to proteolytic activity [Damon et al., *J. Cell. Physiol.*, 138:221–226 (1989); Mueller et al., *J. Cell. Physiol.*, 140:439–448 (1989); Rosengart et al., *Biochem. Biophys. Res. Commun.*, 152:432–440 (1988)] and denaturation [Copeland et al., *Arch. Biochem. Biophys.*, 289:53–61 (1994)] when bound to heparin. Coincubation of HGF with soluble heparin and other heparin-like molecules has been reported to promote dimerization/oligomerization of HGF and to potentiate HGF mitogenic activity. [see, e.g., WO 95/07097 published Mar. 16, 1995; Zioncheck et al., *J. Biol. Chem.*, 270:16871–16878 (1995)].

Mizuno et al. describe some experiments which attempted to locate heparin-binding sites within the HGF molecule [Mizuno et al., *J. Biol. Chem.*, 269:1131–1136 (1994)]. Mizuno et al. constructed variously deleted mutant HGFs [d-K1 (deletion of first kringle domain); d-K2 (deletion of second kringle domain); d-K3 (deletion of third kringle domain); d-K4 (deletion of fourth kringle domain); d-beta (deletion of beta chain); d-H (deletion of N-terminal hairpin loop); and HK1K2 (consisting of N-terminal hairpin loop and the first and second kringle domains)] and examined their respective binding to an immobilized heparin column. The reference reports that the d-H and d-K2 mutants exhibited decreased binding to heparin affinity columns, while the native HGF and the other constructed HGF mutants tightly bound to the heparin columns.

Various biological activities have been described for HGF and its c-Met receptor [see, generally, Chan et al., *Hepatocyte Growth Factor-Scatter Factor (HGF-SF) and the C-Met Receptor*, Goldberg and Rosen, eds., Birkhauser Verlag-Basel (1993), pp. 67–79]. It has been observed that levels of HGF increase in the plasma of patients with hepatic failure [Gohda et al., supra] and in the plasma [Lindroos et al., *Hepatol.*, 13:743–750 (1991)] or serum [Asami et al., *J. Biochem.*, 109:8–13 (1991)] of animals with experimentally induced liver damage. The kinetics of this response are usually rapid, and precedes the first round of DNA synthesis during liver regeneration. HGF has also been shown to be a mitogen for certain cell types, including Schwann cells, melanocytes, renal tubular cells, keratinocytes, certain endothelial cells and cells of epithelial origin [Matsumoto et al., *Biochem. Biophys. Res. Commun.*, 176:45–51 (1991); Igawa et al., *Biochem. Biophys. Res. Commun.*, 174:831–838 (1991); Han et al., *Biochem.*, 30:9768–9780 (1991); Rubin et al., *Proc. Natl. Acad. Sci. USA*, 88:415–419 (1991); Krasnoselsky et al., *J. Neuroscience*, 14:7284–7290 (1994)]. Both HGF and the c-Met protooncogene have been postulated to play a role in microglial reactions to CNS injuries [DiRenzo et al., *Oncogene*, 8:219–222 (1993)].

HGF can also act as a "scatter factor", an activity that promotes the dissociation of epithelial and vascular endothelial cells in vitro [Stoker et al., *Nature*, 327:239–242 (1987); Weidner et al., *J. Cell Biol.*, 111:2097–2108 (1990); Naldini et al., *EMBO J.*, 10:2867–2878 (1991); Giordano et al., *Proc. Natl. Acad. Sci. USA*, 90:649–653 (1993)]. Moreover, HGF has recently been described as an epithelial morphogen [Montesano et al., *Cell*, 67:901–908 (1991)].

Therefore, HGF has been postulated to be important in tumor invasion [Comoglio, *Hepatocyte Growth Factor-Scatter Factor (HGF-SF) and the C-Met Receptor*, Goldberg and Rosen, eds., Birkhauser Verlag-Basel (1993), pp. 131–165]. Bellusci et al., *Oncogene*, 9:1091–1099 (1994) report that HGF can promote motility and invasive properties of NBT-II bladder carcinoma cells.

c-Met RNA has been detected in several murine myeloid progenitor tumor cell lines [Iyer et al., *Cell Growth and Differentiation*, 1:87–95 (1990)]. Further, c-Met is expressed in various human solid tumors [Prat et al., *Int. J. Cancer*, supra]. Overexpression of the c-Met oncogene has also been suggested to play a role in the pathogenesis and progression of thyroid tumors derived from follicular epithelium [DiRenzo et al., *Oncogene*, 7:2549–2553 (1992)]. Chronic c-Met/HGF receptor activation has also been observed in certain malignancies [Cooper et al., *EMBO J.*, 5:2623–2628 (1986); Giordano et al., *Nature*, 339:155–156 (1989)].

SUMMARY OF THE INVENTION

The invention provides HGF receptor agonists which are capable of specifically binding to a HGF receptor. Preferred HGF receptor agonists are capable of substantially enhancing mitogenic, motogenic or other biological activity of HGF or HGF receptor activation, and thus are useful in the treatment of various diseases and pathological conditions, including pathological conditions of the liver. In one embodiment of the invention, the HGF receptor agonist is an antibody. Preferably, this agonist is a monoclonal antibody.

The invention also provides hybridoma cell lines which produce HGF receptor agonistic monoclonal antibodies.

The invention also provides compositions comprising one or more HGF receptor agonists and a pharmaceutically-acceptable carrier. In one embodiment, such composition may be included in an article of manufacture or kit.

The invention also provides methods of gene therapy comprising exposing hepatocytes to an effective amount of a HGF receptor agonist to stimulate hepatocyte proliferation and introducing a desired genetic material into the proliferating hepatocytes.

The invention further provides methods for treating pathological liver conditions comprising administering to a mammal an effective amount of a HGF receptor agonist. The HGF receptor agonist alone may be administered to the mammal, or alternatively, may be administered to the mammal in combination with other therapeutic agents.

It is believed that the agonists can be used as therapeutic, as well as diagnostic, agents. Given the ability of, for instance, monoclonal antibody 3D6 (described herein) to stimulate hepatocyte proliferation, the antibody agonist may be employed as a therapy for acute liver failure. As a diagnostic agent, such an agonist may be used, for example, to detect overexpression of c-Met in mammalian tissues.

BRIEF DESCRIPTION OF THE DRAWINGS

FIGS. 1A and 1B show the results of an in vitro proliferation assay of mink lung cells responding to 3D6 monoclonal antibody.

FIG. 2 shows a graph illustrating mean fluorescence intensity of hepatocytes incubated with 6E10 and 3D6 antibodies and analyzed by flow cytometry.

FIG. 3 shows a graph illustrating the pharmacokinetics (serum concentration/time curve) of 3D6 antibody in ferrets (2 mg/kg single dose).

FIGS. 4A–4C show: the mean hepatocyte proliferation index (4A); the mean percentage LW/BW ratio (4B); and mean serum albumin concentration (4C) in 3D6 and 6E10 antibody treated ferrets at 24, 48 and 72 hours.

FIGS. 5A–5C show: BrdU labeling in ferret liver tissues 24 hours after 6E10 or 3D6 antibody treatment (5A and 5B); a higher magnification of FIG. 5B, illustrating dividing hepatocytes (5C).

FIGS. 6A–6C show: a H&E stained section of pancreas tissue from a ferret at 48 hours after 3D6 antibody treatment (6A); a BrdU stained section of pancreas tissue from the ferret at 48 hours after 3D6 antibody treatment (6B); a graph illustrating the acinar cell proliferation index for the 6E10 and 3D6 antibody treated ferrets at 24, 48 and 72 hours.

FIGS. 7A–7B show: a H&E stained section of autonomic nerve tissue from a ferret at 48 hours after 3D6 antibody treatment (7A); a BrdU stained section of autonomic nerve tissue from a ferret at 48 hours after 3D6 antibody treatment (7B).

FIG. 8 shows a photograph of a SDS-PAGE gel of ferret samples tested for tyrosine phosphorylation of ferret liver c-Met. All samples were blotted with rabbit anti-phosphotyrosine. Lanes 1 and 5 received excipient alone; Lanes 2 and 6—HGF treated samples; Lanes 3 and 7—3D6 treated samples; Lanes 4 and 8—6E10 treated samples. Each of the paired samples represents a single animal. Lanes 1–4 were immunoprecipitated with rabbit anti-c-Met and Lanes 5–8 were immunoprecipitated with anti-phosphotyrosine (4G10).

FIG. 9 shows the induction of c-Met phosphorylation by 3D6 antibody on A549 cells, as determined in a sandwich ELISA.

DETAILED DESCRIPTION OF THE INVENTION

I. Definitions

As used herein, the terms "hepatocyte growth factor" and "HGF" refer to a growth factor typically having a structure with six domains (finger, Kringle 1, Kringle 2, Kringle 3, Kringle 4 and serine protease domains) and having the property of binding to a HGF receptor, as defined below. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified or isolated from a natural source, chemically synthesized or recombinantly produced. Human HGF is encoded by the cDNA sequence published by Miyazawa et al., 1989, supra, or Nakamura et al., 1989, supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The HGF of the invention preferably has at least about 80% sequence identity, more preferably at least about 90% sequence identity, and even more preferably, at least about 95% sequence identity with a native mammalian HGF. The terms "hepatocyte growth factor" and "HGF" specifically include the delta5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as $p_{190}$MET. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence identity, and more preferably at least about 75% sequence identity with any domain of the human c-Met amino acid sequence published in Rodrigues et al., *Mol. Cell. Biol.*, 11:2962–2970 (1991); Park et al., *Proc. Natl. Acad. Sci.*, 84:6379–6383 (1987); or Ponzetto et al., *Oncogene*, 6:553–559 (1991).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the HGF receptor agonist natural environment will not be present. Ordinarily, however, isolated polypeptide will be prepared by at least one purification step. Homogeneity here means less than about 5% contamination with other source proteins and polypeptides.

An "isolated" HGF receptor agonist nucleic acid molecule is a nucleic acid molecule that is identified and separated from at least one contaminant nucleic acid molecule with which it is ordinarily associated in the natural source of the HGF receptor agonist nucleic acid. An isolated HGF receptor agonist nucleic acid molecule is other than in the form or setting in which it is found in nature. Isolated HGF receptor agonist nucleic acid molecules therefore are distinguished from the HGF receptor agonist nucleic acid molecule as it exists in natural cells. However, an isolated HGF receptor agonist nucleic acid molecule includes HGF receptor agonist nucleic acid molecules contained in cells that ordinarily express HGF receptor agonist where, for example, the nucleic acid molecule is in a chromosomal location different from that of natural cells.

The terms "amino acid" and "amino acids" refer to all naturally occurring L-α-amino acids. This definition is meant to include norleucine, ornithine, and homocysteine. The amino acids are identified by either the single-letter or three-letter designations:

| Asp | D | aspartic acid | Ile | I | isoleucine |
|-----|---|---------------|-----|---|------------|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

The term "heparin" is used in a broad sense and refers to a heterogeneous group of sulfated, straight-chain anionic mucopolysaccharides, often referred to as glycosaminoglycans. Although others may be present, the main sugars in heparin are: α-L-iduronic acid 2-sulfate, 2-deoxy-2-sulfamino-α-glucose 6-sulfate, β-D-glucuronic acid, 2-acetamido-2-deoxy-α-D-glucose, and L-iduronic acid. These and optionally other sugars are typically joined by glycosidic linkages. The molecular weight of heparin typically varies from about 6,000 to about 20,000 Da depending on the source and the method of molecular weight determination. Heparin is a native constituent of various cells and tissues, especially liver and lung, in several mammalian species.

The term "heparin-independent" when used herein describes HGF receptor agonists which have substantially reduced ability to bind heparin or are unable to bind heparin, or heparin-like glycosaminoglycans, including heparan sulfate and proteoglycans. Determination of whether a HGF receptor agonist is heparin-independent can be determined by the skilled artisan without undue experimentation.

The terms "agonist" and "agonistic" when used herein refer to or describe a molecule which is capable of, directly or indirectly, substantially inducing, promoting or enhancing HGF biological activity or HGF receptor activation.

The terms "antagonist" and "antagonistic" when used herein refer to or describe a molecule which is capable of, directly or indirectly, substantially counteracting, reducing or inhibiting HGF biological activity or HGF receptor activation.

The term "HGF biological activity" when used herein refers to any mitogenic, motogenic or morphogenic activities of HGF or any activities occurring as a result of HGF binding to a HGF receptor. The term "HGF receptor activation" refers to HGF receptor dimerization or HGF receptor-induced tyrosine kinase activity. HGF receptor activation may occur as a result of HGF binding to a HGF receptor, but may alternatively occur independent of any HGF binding to a HGF receptor. HGF biological activity may, for example, be determined in an in vitro or in vivo assay of hepatocyte growth promotion. Adult rat hepatocytes in primary culture have been used to test the effect of HGF on hepatocyte proliferation. Accordingly, the effect of a HGF receptor agonist can be determined in an assay suitable for testing the ability of HGF to induce DNA synthesis of rat hepatocytes in primary cultures. Human or ferret hepatocytes can be cultured similarly to the methods established for preparing primary cultures of normal rat hepatocytes. Alternatively, the effect of a HGF receptor agonist can be determined in an assay suitable for testing the ability of HGF to induce DNA synthesis in other types of cells expressing HGF receptor(s), such as mink lung cells or ferret hepatocytes described in the Examples below. DNA synthesis can, for example, be assayed by measuring incorporation of $^3$H-thymidine into DNA. The effectiveness of the HGF receptor agonist can be determined by its ability to promote or enhance proliferation and incorporation of the $^3$H-thymidine into DNA. The effect of HGF receptor agonists can also be tested in vivo in animal models.

The term "antibody" is used herein in a broad sense and includes intact immunoglobulin or antibody molecules, polyclonal antibodies, multispecific antibodies (i.e., bispecific antibodies formed from at least two intact antibodies) and immunoglobulin fragments (such as Fab, F(ab')$_2$, or Fv), so long as they exhibit any of the desired agonistic properties described herein. Antibodies are typically proteins or polypeptides which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains [Chothia et al., *J. Mol. Biol.*, 186:651–663 (1985); Novotny and Haber, *Proc. Natl. Acad. Sci. USA*, 82:4592–4596 (1985)]. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, delta, epsilon, γ, and μ, respectively.

"Antibody fragments" comprise a portion of an intact antibody, generally the antigen binding or variable region of the intact antibody. Examples of antibody fragments include Fab, Fab', F(ab')2, and Fv fragments, diabodies, single chain antibody molecules, and multispecific antibodies formed from antibody fragments.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies [see Kabat, E. A. et al., *Sequences of Proteins of Immunological Interest*, National Institutes of Health, Bethesda, Md. (1987)]. The constant domains are not involved directly in binding an antibody to an antigen, but exhibit various effector functions, such as participation of the antibody in antibody-dependent cellular toxicity.

The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired agonistic activity [U.S. Pat. No. 4,816,567; Morrison et al., *Proc. Natl. Acad. Sci. USA*, 81:6851–6855 (1984)].

The terms "treating," "treatment," and "therapy" as used herein refer to curative therapy, prophylactic therapy, and preventative therapy.

The term "mammal" as used herein refers to any animal classified as a mammal, including humans, cows, horses, dogs and cats. In a preferred embodiment of the invention, the mammal is a human.

II. Compositions and Methods of the Invention

In one embodiment of the invention, HGF receptor agonists are provided. Non-limiting examples of HGF receptor agonists include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like.

In another preferred embodiment of invention, the HGF receptor agonists of the invention are HGF receptor antibodies. For instance, the agonistic antibodies may be polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Preferably, the immunizing agent includes the c-Met polypeptide or a fusion protein thereof. It may be useful to conjugate the immunizing agent to a protein known to be immunogenic in the mammal being immunized. Examples of such immunogenic proteins which may be employed include but are not limited to keyhole limpet hemocyanin, serum albumin, bovine thyroglobulin, and soybean trypsin inhibitor. An aggregating agent such as alum may also be employed to enhance the mammal's immune response. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for HGF receptor antibody titer. If desired, the mammal can be boosted until the antibody titer increases or plateaus.

The agonistic antibodies of the invention may, alternatively, be monoclonal antibodies. Agonistic monoclonal antibodies of the invention may be prepared using hybridoma methods, such as those described by Kohler and Milstein, *Nature*, 256:495–497 (1975). In a hybridoma method, a mouse or other appropriate host animal, is typically immunized (such as described above) with an immunizing agent to elicit lymphocytes that produce or are capable of producing antibodies that will specifically bind to the immunizing agent. Alternatively, the lymphocytes may be immunized in vitro.

Preferably, the immunizing agent includes the c-Met polypeptide or a fusion protein thereof. The immunizing agent may alternatively comprise a fragment or portion of HGF or a HGF receptor having one or more amino acid residues that participate in the binding of HGF to its receptor. In a more preferred embodiment, the immunizing agent comprises an extracellular domain of c-Met fused to an IgG sequence, such as described in Example 1.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. An example of such a murine myeloma cell line is P3X63AgU.1, described in Example 1 below. Human myeloma and mouse-human heteromyeloma cell lines also have been described for the production of human monoclonal antibodies [Kozbor, *J. Immunol.*, 133:3001–3005 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against a HGF receptor. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below. The binding affinity of the monoclonal antibody can, for example, be determined by the Scatchard analysis of Munson and Pollard, *Anal. Biochem.*, 107:220–239 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody comprising one antigen-combining site having specificity for a HGF receptor and another antigen-combining site having specificity for a different antigen.

In a more preferred embodiment, the monoclonal antibodies have the same biological characteristics as the monoclonal antibodies secreted by the hybridoma cell line deposited under American Type Culture Collection Accession No. ATCC HB-12093. The term "biological characteristics" is used to refer to the in vitro and/or in vivo activities or properties of the monoclonal antibody, such as the ability to specifically bind to c-Met or to substantially induce or enhance c-Met activation. As disclosed in the present specification, the 3D6 monoclonal antibody (ATCC HB-12093) is characterized as having a relatively long serum half-life in vivo, being heparin-independent, and principally affecting induction of hepatocyte proliferation and liver growth. The monoclonal antibody will also preferably bind to substantially the same epitope as the 3D6 antibody disclosed herein. This can be determined by conducting various assays, such as described herein and in the Examples. For instance, to determine whether a monoclonal antibody has the same specificity as the 3D6 antibody specifically disclosed (i.e., the antibody having the ATCC deposit No. HB-12093), one can compare activity in a c-Met tyrosine phosphorylation assay, such as described in the Examples below.

The agonistic antibodies of the invention may also comprise monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment.

Pepsin treatment yields an F(ab')$_2$ fragment that has two antigen combining sites and is still capable of cross-linking antigen.

The Fab fragments produced in the antibody digestion also contain the constant domains of the light chain and the first constant domain (CH$_1$) of the heavy chain. Fab' fragments differ from Fab fragments by the addition of a few residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

In addition to the agonistic antibodies described above, it is contemplated that chimeric or hybrid agonistic antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

The agonistic antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.* 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody [Sims et al., *J. Immunol.*, 151:2296–2308 (1993); Chothia and Lesk, *J. Mol. Biol.*, 196:901–917 (1987)]. Another method uses a particular framework derived from the consensus sequence of all human antibodies of a particular subgroup of light or heavy chains. The same framework may be used for several different humanized antibodies [Carter et al., *Proc. Natl. Acad. Sci. USA*, 89:4285–4289 (1992); Presta et al., *J. Immunol.*, 151:2623–2632 (1993)].

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art.

Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding [see, WO 94/04679 published Mar. 3, 1994].

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J$_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge [see, e.g., Jakobovits et al., *Proc. Natl. Acad. Sci. USA*, 90:2551–2555 (1993); Jakobovits et al., *Nature*, 362:255–258 (1993); Bruggemann et al., *Year in Immuno.*, 7:33–40 (1993)]. Human antibodies can also be produced in phage display libraries [Hoogenboom and Winter, *J. Mol. Biol.*, 227:381–388 (1991); Marks et al., *J. Mol. Biol.*, 222:581–597 (1991)]. The techniques of Cole et al. and Boerner et al. are also available for the preparation of human monoclonal antibodies (Cole et al., *Monoclonal Antibodies and Cancer Therapy*, Alan R. Liss, p. 77–96 (1985) and Boerner et al., *J. Immunol.*, 147(1):86–95 (1991)].

In another embodiment of the invention, methods for treating pathological conditions of the liver are provided.

Pathological liver conditions contemplated by the invention include acute liver failure, alcoholic hepatitis, and acute or chronic hepatitis (preferably in the absence of cirrhosis). Diagnosis of such conditions are within the routine skill of the medical practitioner or clinician. In the methods, HGF receptor agonist is administered to a mammal, alone or in combination with still other therapeutic techniques.

The agonist is preferably administered to the mammal in a pharmaceutically-acceptable carrier. Suitable carriers and their formulations are described in *Remington's Pharmaceutical Sciences*, 16th ed., 1980, Mack Publishing Co., edited by Oslo et al. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the agonist, which matrices are in the form of shaped articles, e.g., films, liposomes or microparticles. It will be apparent to those persons skilled in the art that certain carriers may be more preferable depending upon, for instance, the route of administration and concentration of agonist being administered.

The agonist can be administered to the mammal by injection (e.g., intravenous, intraperitoneal, subcutaneous, intramuscular, intraportal), or by other methods such as infusion that ensure its delivery to the bloodstream in an effective form. The agonist may also be administered by isolated perfusion techniques, such as isolated liver perfusion, to exert local therapeutic effects. Local or intravenous injection is preferred.

Effective dosages and schedules for administering the agonist may be determined empirically, and making such determinations is within the skill in the art. Those skilled in the art will understand that the dosage of agonist that must be administered will vary depending on, for example, the mammal which will receive the agonist, the route of administration, the particular type of agonist used and other drugs being administered to the mammal. Guidance in selecting appropriate doses for antibody agonists is found in the literature on therapeutic uses of antibodies, e.g., *Handbook of Monoclonal Antibodies*, Ferrone et al., eds., Noges Publications, Park Ridge, N.J., (1985) ch. 22 and pp. 303–357; Smith et al., *Antibodies in Human Diagnosis and Therapy*, Haber et al., eds., Raven Press, New York (1977) pp. 365–389. A typical daily dosage of the agonist used alone might range from about 1 µg/kg to up to 100 mg/kg of body weight or more per day, depending on the factors mentioned above.

The agonist may also be administered to the mammal in combination with effective amounts of one or more other therapeutic agents. The agonist may be administered sequentially or concurrently with the one or more other therapeutic agents. The amounts of agonist and therapeutic agent depend, for example, on what type of drugs are used, the pathological condition being treated, and the scheduling and routes of administration but would generally be less than if each were used individually.

Following administration of agonist to the mammal, the mammal's physiological condition can be monitored in various ways well known to the skilled practitioner.

In another embodiment of the invention, methods of gene therapy are provided. In the methods, mammalian hepatocytes are exposed to an effective amount of a HGF receptor agonist to stimulate hepatocyte proliferation and a desired genetic material is introduced into the proliferating hepatocytes. The hepatocytes may be exposed to the HGF receptor agonist in vivo or ex vivo. In a preferred embodiment, the hepatocytes are exposed to an effective amount of 3D6 antibody. Typically, the desired genetic material will be a nucleic acid encoding a polypeptide or protein of clinical interest. The desired genetic material may be, for instance, a gene encoding a protein which the mammal is in need of or deficient in. The gene therapy methods contemplated by the invention, however, are not intended to be limited to introducing genetic material which directly or indirectly influences the physiology or health of the liver cells or tissue. By way of example, the genetic material may be a nucleic acid encoding LDL receptor and such nucleic acid can be introduced into the proliferating hepatocytes of a mammal having LDL receptor deficiency.

There are two major approaches to delivering the genetic material (typically contained in a vector) into the mammal's hepatocytes—in vivo and in vitro. For in vivo delivery, the genetic material may be injected or delivered directly into the mammal, preferably into the liver tissue. The HGF receptor agonist may be administered to the mammal via various methods, such as described above. For in vitro delivery, the mammal's hepatocytes or liver tissue are surgically removed from the mammal's body, such as by a partial hepatectomy, the hepatocytes are exposed to the HGF receptor agonist to stimulate cell proliferation, and the genetic material is introduced into the hepatocytes. The in vitro treated hepatocytes are then administered or transplanted back into the mammal.

There are a variety of techniques available and known in the art for introducing the desired genetic material into the proliferating hepatocytes. The techniques will vary depending upon, for instance, whether the genetic material is delivered into hepatocytes in vitro or in vivo. Techniques suitable for the transfer of the genetic material into the hepatocytes in vitro include the use of vectors, liposomes, electroporation, microinjection, cell fusion, DEAE-dextran, and calcium phosphate precipitation. A commonly used vector for in vitro delivery of genetic material is a retrovirus. In vivo gene delivery techniques include transfection with viral vectors (such as adenovirus) and lipid-based systems. When liposomes are employed, proteins which bind to cell surface protein associated with endocytosis may be used for targeting and/or uptake. For a review of several gene delivery protocals, see Anderson et al., *Science*, 256:808–813 (1992); WO 93/25673.

In still another embodiment of the invention, methods for employing the agonists in diagnostic assays are provided. For instance, the agonists may be employed in diagnostic assays to detect overexpression of HGF receptor in specific cells and tissues. Various diagnostic assay techniques known in the art may be used, such as in vivo imaging assays, in vitro competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The agonists used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, bet-galactosidase or horseradish peroxidase. Any method known in the art for conjugating the agonist to the detectable moiety may be employed, including those methods described by Hunter et al., *Nature*, 144:945 (1962); David et al., *Biochemistry*, 13:1014–1021 (1974); Pain et al., *J. Immunol. Meth.*, 40:219–230 (1981); and Nygren, *J. Histochem. and Cytochem.*, 30:407–412 (1982).

Additionally, agonistic antibodies of the invention can be used to immunopurify HGF receptor(s).

In a further embodiment of the invention, there are provided articles of manufacture and kits containing materials useful for gene therapy, treating pathological liver conditions or detecting or purifying HGF receptor. The article of manufacture comprises a container with a label. Suitable containers include, for example, bottles, vials, and test tubes. The containers may be formed from a variety of materials such as glass or plastic. The container holds a composition having an active agent which is effective for gene therapy, treating pathological liver conditions or for detecting or purifying HGF receptor. The active agent in the composition is a HGF receptor agonist and preferably, comprises monoclonal antibodies specific for c-Met. Even more preferably, the active agent comprises 3D6 monoclonal antibody. The label on the container indicates that the composition is used for gene therapy, treating pathological liver conditions or detecting or purifying HGF receptor, and may also indicate directions for either in vivo or in vitro use, such as those described above.

The kit of the invention comprises the container described above and a second container comprising a buffer. It may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All reference citations herein are incorporated by reference.

EXAMPLE 1

Preparation of Monoclonal Antibody 3D6

Balb/c mice (obtained from Charles River Laboratories) were immunized by injecting 2.5 µg/50 µl c-Met-IgG fusion protein (diluted in MPL-TDM adjuvant purchased from Ribi Immunochemical Research Inc., Hamilton, Mont.) five times into each hind foot pad. Injections were administered on Day 0 and Days 56, 63, 66 and 73. The c-Met-IgG fusion protein (including the extracellular domain of c-Met fused to a human IgGi heavy chain) was constructed essentially as described by Mark et al., *J. Biol. Chem.*, 267:26166–26171 (1992) and produced in Chinese hamster ovary (CHO) cells. The c-Met-IgG was subsequently purified in a single step using affinity chromatography on immobilized Protein A (Bioprocessing, Inc., Princeton, N.J.), using an elution scheme modified from Chamow et al., *J. Immunol.*, 153:4268–4280 (1994). Culture supernatant was loaded onto a Protein A column equilibrated in 20 mM Tris, pH 7.4, 0.15 M NaCl. The column was washed, first with equilibration buffer, then with equilibration buffer containing 0.5 M tetramethylammonium chloride, to remove non-specifically bound protein. c-Met-IgG was eluted with 20 mM Tris, pH 7.4, 3.5 M $MgCl_2$. This c-Met-IgG eluate was concentrated and exchanged into 20 mM Tris, pH 7.4, 0.15 M NaCl by gel filtration on Sephadex G25 to a final concentration of about 2–4 mg/ml.

On Day 77, popliteal lymph nodes were removed from the mice and a single cell suspension was prepared in DMEM media (obtained from Biowhitakker Corp.) supplemented with 1% penicillin-streptomycin. The lymph node cells were then fused with murine myeloma cells P3X63AgU.1 (ATCC CRL 1597) using 35% polyethylene glycol and cultured in 96-well culture plates. Hybridomas resulting from the fusion were selected in HAT medium. Ten days after the fusion, hybridoma culture supernatants were screened in an ELISA to test for the presence of monoclonal antibodies binding to the c-Met-IgG fusion protein.

In the ELISA, 96-well microtiter plates (Nunc) were coated by adding 50 µl of 2 µg/ml goat anti-human IgG Fc (purchased from Cappel Laboratories) to each well and incubating at 4° C. overnight. The plates were then washed three times with distilled water. The wells in the microtiter plates were blocked with 200 µl of 2% bovine serum albumin and incubated at room temperature for 1 hour. The plates were then washed again three times with distilled water.

After the washing step, 100 µl of 0.4 µg/ml c-Met-IgG fusion protein (as described above) was added to each well. The plates were incubated for 1 hour at room temperature on a shaker apparatus, followed by washing three times with distilled water.

Then, 100 µl of the hybridoma supernatants was added to designated wells. 100 µl of P3X63AgU.1 myeloma cell conditioned medium was added to other designated wells as controls. The plates were incubated at room temperature for 1 hour on a shaker apparatus and then washed three times with distilled water.

Next, 50 µl HRP-conjugated goat anti-mouse IgG Fc (purchased from Cappel Laboratories), diluted 1:1000 in assay buffer (0.56 bovine serum albumin, 0.05% Tween-20, 0.01% Thimersol in PBS), was added to each well and the plates incubated for 1 hour at room temperature on a shaker apparatus. The plates were washed three times with distilled water, followed by addition of 50 µl of substrate (5 mg OPD, 12.5 ml PBS, 5 µl $H_2O_2$) to each well and incubation at room temperature for 10 minutes. The reaction was stopped by adding 50 µl of 2 N $H_2SO_4$ to each well, and absorbance at 490 nm was read in an automated microtiter plate reader.

Of 912 hybridoma supernatants screened in the ELISA, 24 supernatants tested positive (calculated as approximately 2 times above background). The supernatants testing positive in the ELISA were further analyzed by FACS analysis using BAF3 transfected cells expressing human c-Met. The transfected BAF3 cells were constructed as follows. An expression plasmid was prepared by inserting a full-length cDNA for human c-Met (described as pOK met cDNA in Rodrigues et al., supra) into a pRK5.tk.neo vector [de Sauvage et al., *Nature*, 369:533–538 (1994); Gorman, *DNA Cloning: A New Approach*, 2:143–190 (IRL Washington 1985)]. The resulting plasmid was linearized and transfected into the IL-3 dependent cell line, BaF3 [Palacios et al., *Cell*, 41:727–734 (1985)] by electroporation (800 microfarad, 250 V, BRL electroporator). Selection of transfectants was performed by culturing the cells for 2–3 weeks in the presence of 2 mg/ml G418. One of the selected transfectant cell lines, referred to as BaF3-hmet.8, was confirmed by Western blotting to express c-Met. BaF3-hmet.8 also tested positive for response to HGF in a proliferation assay measuring incorporation of $^3$H-thymidine. Neither the parental BaF3 cells nor any cells derived by transfection with the pRK5.tk.neo vector alone were found to express c-Met or respond to HGF in the proliferation assay.

The BaF3-hmet.8 cells were passaged in RPMI medium supplemented with 106 fetal bovine serum, 5% WEHI-conditioned medium (as a source of IL-3) and 2 mM glutamine. Prior to conducting the assay, the cells were washed twice with assay medium (RPMI medium supplemented with 10% fetal bovine serum) and resuspended in assay medium to a concentration of $5 \times 10^4$ cells/ml.

The hybridomas were cloned twice by limiting dilution and then further characterized for agonistic properties. The 3D6 monoclonal antibody was selected and purified from ascites using a protein G affinity column, filter sterilized, and stored at 4° C. prior to use. Endotoxin activity (EU), as determined by the Limulus Amebocyte Lysate assay, was less than 1 EU/mg.

EXAMPLE 2

In vitro Assay Using Mink Lung Cell Line

Mink lung cells (Mv 1 Lu, ATCC CCl 64) were passaged in MEM supplemented with 10% fetal bovine serum, 2 mM glutamine, 100 U/ml penicillin, and 100 µg/ml streptomycin. Prior to conducting the assay, the mink lung cells were released from the culture flask with trypsin-EDTA (Sigma), washed twice with assay medium (DME/F12 medium supplemented with 1 mg/ml BSA and 2 mM glutamine), resuspended in assay medium to a concentration of $1 \times 10^5$ cells/ml, and seeded into 96 well plates.

Recombinant human HGF (rhuHGF) was produced in CHO cells using a procedure modified from Naka et al., *J. Biol. Chem.*, 267:20114–20119 (1992). rhuHGF-transfected cells were grown in a 400 L bioreactor in medium containing 2% fetal bovine serum for 8 days. Culture supernatant containing rhuHGF was concentrated and clarified, then conditioned by the addition of solid NaCl to 0.3 M. rhuHGF was then purified in a single step using cation exchange chromatography. Conditioned, concentrated culture supernatant was loaded onto a column of S-Sepharose Fast Flow equilibrated in 20 mM Tris, pH 7.5, 0.3 M NaCl. After washing out unbound protein, rhuHGF was eluted in a linear gradient from 20 mM Tris, pH 7.5, 0.3 M NaCl to 20 mM Tris, pH 7.5, 1.2 M NaCl. rhuHGF-containing fractions were pooled based on SDS-PAGE analysis. The S Sepharose Fast Flow pool was concentrated and exchanged into 20 mM Tris, pH 7.5, 0.5 M NaCl by gel filtration on Sephadex G25 to a final concentration of about 3–5 mg/ml. A rhuHGF stock solution was then prepared by diluting the rhuHGF in assay buffer (0.5% bovine serum albumin, 0.05% Tween-20, 0.01% Thimersol in PBS) to a concentration of 10 µg/ml. A stock solution of c-Met-IgG (described in Example 1) in assay buffer was prepared to a concentration of 20 µg/ml.

An IgG1 mouse monoclonal antibody, 3C1 (Genentech, Inc.), that recognizes human c-Met, but not mink c-Met, was used as a negative control. The 3D6 (as described in Example 1) and 3C1 antibodies were diluted in assay medium at varying concentrations, and 100 µl of the antibody preparations (or 100 µl of rhuHGF or c-Met-IgG) was then added to designated wells in the 96 well plates to yield the final concentrations identified in FIGS. 1A and 1B. The plates were incubated at 37° C. in 5% $CO_2$ for 16 hours.

Next, 1 µCi $^3$H-thymidine was added to each well, and the plates were incubated for 24 hours at 37° and 5% $CO_2$. The cells were harvested onto Packard Unifilter GF/B plates with a Packard Filtermate 196 cell harvestor. The amount of radioactivity incorporated into the DNA was then quantitated in a Packard Top-Count microplate scintillation counter.

FIGS. 1A and 1B show the results. Statistical analyses were tested by Analysis of Variance ("ANOVA"). DNA synthesis was significantly increased above baseline in the presence of HGF and 3D6. ($P<0.05$). A maximal response was achieved with 3D6 at a concentration of 100 ng/ml. The stimulatory effects of HGF and 3D6 were specifically inhibited in a dose-dependent manner by soluble c-Met-IgG. There was no increase over background in DNA synthesis when cells were cultured in the presence of the control antibody, 3C1. Baseline inhibition of mink lung cell proliferation by c-Met-IgG resulted from inhibition of low amounts of HGF in the culture, secreted in an autocrine manner by mink lung cells (data not shown).

EXAMPLE 3

In vitro Assay Using Primary Ferret Heoatocytes

Young male ferrets (450–920 g) were obtained from Marshall farms, Syracuse, N.Y. All the animals were castrated and descented prior to dispatch. The animals were group housed under 12 hour light/dark cycles and received a standard laboratory ferret chow. All experiments were conducted under the current guidelines and were approved by the institutional ACUC.

Primary ferret hepatocytes were isolated by a modified recirculating two-stage in situ collagenase perfusion technique [Seglen, *Meth. Cell Biol.*, 13:29–83 (1976)], using 0.05% collagenase type IV in Earle's buffered salt solution. Livers were perfused at 25 ml/minute for 10–15 minutes. After removal, the liver was minced with scissors, filtered over gauze and the cell suspension was passed through 35 micron nylon mesh (obtained from Small Parts, Inc., Miami Lakes, Fla.). Prior to use, cells were washed and pelleted at 50 g, three times in Leibovitz 15 medium (Gibco).

The isolated hepatocytes ($1 \times 10^6$/ml) were incubated in L15 medium containing 10% fetal calf serum for 1 hour at room temperature in the presence or absence of 10 µg/ml 3D6 antibody (described in Example 1) or 6E10 (an IgG1 mouse monoclonal antibody that recognizes the gp120 glycoprotein of HIV1, used as a negative control; Genentech, Inc.). The cells were then washed three times and incubated for 1 hour with R-phycoerythrin conjugated goat anti-mouse antibody (Jackson Immunoresearch Laboratories, Inc., West Grove, Pa.) (1 µg/ml). After washing, propidium iodide was added to allow exclusion of dead cells. Cell viability, which was consistently 80–90%, and antibody binding to hepatocytes was analyzed by flow cytometry.

As shown in FIG. 2, incubation with 3D6, but not with 6E10, induced a log shift in mean fluorescence intensity demonstrating that the 3D6 antibody recognizes and binds ferret c-Met receptor.

EXAMPLE 4

In vivo Assay Using Ferrets

Young male ferrets (450–920 g) were obtained from Marshall farms, Syracuse, N.Y. All the animals were castrated and descented prior to dispatch. The animals were group housed under 12 hour light/dark cycles and received a standard laboratory ferret chow. All experiments were conducted under the current guidelines and were approved by the institutional ACUC.

A. Pharmacokinetics

Indwelling polyethylene catheters (commercially available from Becton Dickinson, Sparks, Md.) were implanted under anesthesia into the jugular veins of two ferrets, 5 days prior to dosing. After bolus injection of 3D6 or 6E10 antibodies (as described in Examples 1 and 3, 2 mg/kg), 1 ml blood samples were collected at 0.033, 1, 4, 7, 24, 48 and 123.5 hours. Serum was stored at −20° C. prior to being assayed.

The concentration of the 3D6 and 6E10 antibodies in the ferret serum was then measured using a sandwich ELISA technique. The plates were coated overnight at 4° C. with c-Met-IgG (prepared as described in Example 1, 2 µg/ml). After the blocking, the plates were incubated with diluted ferret sera. The Fc portion of the antibodies was detected with HRP-conjugated goat anti-mouse Fc (Amersham) diluted 1:1000.

Data from each ferret were analyzed by fitting the sum of two exponentials to the unweighted serum concentration versus time data. Derived pharmacokinetic parameters were computed from the coefficients and exponents [Wagner, *J. Pharmacokin. Biopharm.*, 4:443–467 (1976)].

Generally, the 3D6 antibody was well tolerated and stable in serum. The serum concentration-time curve from one of the ferrets after a single 3D6 (2 mg/kg) intravenous dose is shown in FIG. 3. The circles represent the serum concentration data, the solid line represents the pharmacokinetic function that describes the data—Ct=20.6 exp (−0.082t)+

B. Effects on Hepatocyte Proliferation

Conscious animals received a single intravenous bolus of either 3D6 or 6E10, 2 mg/kg in 0.9% saline, into the cephalic vein. A total of 23 animals were included in the study. All animals remained alert and active following administration of either 3D6 or 6E10.

Animals were then euthanised at 24 (3D6, n=3; 6E10, n=2), 48 (3D6, n=6; 6E10, n=6), and 72 (3D6, n=3; 6E10, n=3) hours post-injection of antibodies. In 3D6 treated animals, there was an increase in actual liver weight (data not shown) and in liver weight expressed as a percentage of body weight (FIG. 4B). The difference was significant at 48 and 72 hours. There was no difference in the weight of the kidneys, spleen, heart or brain, when expressed as a percentage of body weight, between the active and placebo treated groups, as shown in Table 1 below. The data in Table 1 are the weights of the spleen, kidneys, heart and brain, expressed as a percentage of body weight, in 3D6 and 6E10 treated animals. The data are given as mean±S.E.

TABLE 1

| Time | Spleen weight/ Body weight % | | Kidney weight/ Body weight % | | Heart weight/ Body weight % | | Brain weight/ Body weight % | |
|---|---|---|---|---|---|---|---|---|
| (hr) | 6E10 | 3D6 | 6E10 | 3D6 | 6E10 | 3D6 | 6E10 | 3D6 |
| 24 | 0.94 ± 0.03 | 0.97 ± 0.14 | 0.54 ± 0.03 | 0.51 ± 0.01 | 0.59 ± 0.03 | 0.62 ± 0.03 | 1.46 ± 0.05 | 1.63 ± 0.10 |
| 48 | 0.98 ± 0.05 | 1.05 ± 0.07 | 0.51 ± 0.01 | 0.52 ± 0.01 | 0.64 ± 0.01 | 0.61 ± 0.02 | 1.52 ± 0.04 | 1.64 ± 0.10 |
| 72 | 0.92 ± 0.04 | 0.82 ± 0.06 | 0.46 ± 0.03 | 0.49 ± 0.02 | 0.59 ± 0.01 | 0.58 ± 0.02 | 1.64 ± 0.06 | 1.71 ± 0.04 |

11.9 exp (−0.0143t). The 3D6 antibody was cleared relatively slowly in both animals (average serum clearance=2 ml/hr). The initial half lives were 1.8 and 8.5 hours, and the terminal half lives 34.7 and 48.5 hours, respectively. The majority of the area under the curve was associated with the terminal half life (76.8–96.5%). The initial volume of distribution was relatively small (62–69 ml/kg), approximately the serum volume; steady state volumes of distribution were approximately 1.7 to 2.5-fold larger. The mean residence There was a statistically significant increase in serum albumin (FIG. 4C), triglyceride and cholesterol levels in 3D6 treated animals, while AST and ALT levels fell. No change was observed in alkaline phosphatase, gamma-GT or bilirubin levels, as shown in Table 2 below. The data in Table 2 shows serum levels of liver function tests in 3D6 and 6E10 treated animals. Results are expressed as mean±S.E. Significant reductions (P<0.05) in levels in 3D6 treated animals are indicated by **.

TABLE 2

| Time | ALT (U/L) | | AST (U/L) | | γ-GT (U/L) | | Alkaline Phosphatase (U/L) | |
|---|---|---|---|---|---|---|---|---|
| (hr) | 6E10 | 3D6 | 6E10 | 3D6 | 6E10 | 3D6 | 6E10 | 3D6 |
| 24 | 189 ± 19 | 139 ± 32** | 98 ± 10 | 56 ± 5** | 6.0 ± 2.1 | 6.3 ± 1.2 | 153 ± 17 | 149 ± 3 |
| 48 | 222 ± 25 | 159 ± 8** | 95 ± 10 | 82 ± 7 | 5.3 ± 1.1 | 7.5 ± 0.8 | 164 ± 17 | 159 ± 8 |
| 72 | 230 ± 8 | 159 ± 7 | 94 ± 3 | 73 ± 4 | 3.0 ± 2.0 | 7.0 ± 1.7 | 185 ± 8 | 141 ± 15 | time in serum was 53 hours. Serum levels of the intact 3D6 antibody were maintained above a concentration of 1 µg/ml for five days; a level, as disclosed above, that induces a maximal level of proliferation of mink lung cells in vitro.

FIG. 4A shows the mean hepatocyte proliferation index (±S.E.). FIG. 4B shows the mean percentage LW/BW ratio (±S.E.). FIG. 4C shows the mean serum albumin concentration (±S.E.) in 3D6 and 6E10 treated animals at 24, 48 and 72 hours. In 3D6 treated animals, the hepatocyte proliferation index was significantly increased at 24 and 48 hours, while there was a corresponding increase in body weight and serum albumin concentration at 48 and 72 hours. Statistically significant changes (P<0.05) are indicated by * in FIGS. 4A–4C.

There was no significant shift in red blood cell, white blood cell or platelet numbers (data not shown).

C. Histology

Bromodeoxyuridine (BrdU) (100 mg/kg) was administered intraperitoneally to all animals 2 hours prior to being euthanised. Animals were exsanguinated under anesthesia by cardiac puncture, and serum and EDTA-treated whole blood samples were collected for biochemistry and hematology examination. Tissues (liver, pancreas, skin, esophagus, stomach, small intestine, colon, heart, lung, kidney, adrenal, thyroid, lymph node, thymus, spleen, brain, skeletal muscle, sciatic nerve, bone and bone marrow) were collected, fixed in 4% buffered formalin and processed for paraffin embedding. Three micron thick sections were cut from each and stained with haematoxylin and eosin ("H & E"), or processed for immunochemistry.

Sections of liver, pancreas, sciatic nerve, kidney, adrenal and small intestine were stained to determine the incorporation of BrdU, using a monoclonal anti-BrdU antibody (Dako) diluted 1:20. Sections were dewaxed in xylene and hydrated through a series of graded alcohols. Endogenous peroxidase was blocked by immersing sections in 1% hydrogen peroxide in distilled water for 30 minutes. After rinsing, sections were trypsinized (0.05%) for 20 minutes at 37° C., then denatured in 95% formamide in 0.15M trisodium citrate for 1 hour at 70° C., washed, blocked in 10% goat serum, diluted in TBS, then incubated with primary antibody overnight at 4° C. Primary antibody was detected with a Vectastain elite ABC kit. Labeled sites were visualized by incubating in 3,3 diaminobenzidine tetrahydrochloride (DAB; Sigma). Sections were counterstained in Mayer's haematoxylin (Sigma), dehydrated through graded alcohols, cleared in xylene and then mounted.

A minimum of 1000 hepatocytes or pancreatic acinar cell nuclei, from a minimum of 15 separate fields in each section, were counted. The BrdU index, expressed as a percentage, was calculated as the number of positively labeled nuclei divided by the total number of hepatocyte or pancreatic acinar nuclei respectively. Only unequivocally stained nuclei were counted as positive.

FIGS. 5A and 5B show BrdU labeling in livers 24 hours after 6E10 (FIG. 5A) or 3D6 (FIG. 5B) administration. A significant increase in positively labeled hepatocytes was observed in 3D6 treated animals. THV indicates a terminal hepatic venule. The hepatic architecture was normal in all animals examined. In animals receiving 3D6, there was an increased hepatocyte proliferation at 24 and 48 hours. The majority of the proliferating hepatocytes were located in zones 2 and 3 of the hepatic acinus. FIG. 5C shows a higher magnification from FIG. 5B, illustrating dividing hepatocytes. There was a corresponding increase in DNA synthesis in hepatocytes as determined by incorporation of BrdU, while no change in DNA synthesis over time was observed in animals treated with the control antibody, 6E10.

The hepatocyte BrdU labeling index (means±S.E.) in 3D6 treated animals reached a peak of 13.8 (±1.6)% at 24 hours and then fell to 3.9 (±0.8)0 at 48 hours and 2.1 (±0.9)% at 72 hours. The BrdU indices at 24 and 48 hours were significantly greater than those of control 6E10 treated animals ($P<0.05$). See FIG. 4A.

FIG. 6 shows a H & E stained section of pancreas (FIG. 6A), with the corresponding area stained for BrdU (FIG. 6B), from an animal 48 hours after 3D6 administration. Mitotic cells of FIG. 6A and BrdU positive cells in FIG. 6B are arrowed. Increased labeling was only observed in acinar cells. The acinar cell proliferation index for 6E10 and 3D6 treated animals is shown in FIG. 6C. A significant ($P<0.05$) increase in acinar cell labeling was observed in 3D6 treated animals at 48 and 72 hours.

Increased proliferation of acinar cells of the exocrine pancreas was observed at 48 and 72 hours after treatment, and was associated with increased DNA synthesis in these cells. (FIGS. 6A and 6B). Pancreata appeared normal and there was no difference in DNA synthesis in pancreatic islet cells between the two groups. In pancreatic acinar cells BrdU labeling was significantly increased in 3D6 treated animals, as compared with 6E10 treated controls at 48 and 72 hours, but not at 24 hours (see FIG. 6C).

FIG. 7 shows an H & E stained section of an autonomic nerve (FIG. 7A), with the corresponding area stained for BrdU (FIG. 7B), from an animal 48 hours after 3D6 administration, mitotic cells of FIG. 7A and BrdU positive cells of FIG. 7B are arrowed. The morphology of the positively labeled cells suggests that they are Schwann cells. Increased proliferation and DNA synthesis was also observed at 48 and 72 hours in cells in peripheral and autonomic nerves (FIGS. 7A and 7B). The cells, which had an elongated spindle cell morphology, had appearances characteristic of Schwann cells.

Sections of skin, esophagus, stomach, small intestine, colon, heart, lung, kidney, adrenal, thyroid, lymph node, thymus, spleen, brain, skeletal muscle, bone and bone marrow were morphologically normal in both groups and showed no evidence of increased cell proliferation.

D. Effect on Tyrosine Phosphorylation of c-Met

The ability of 3D6 to stimulate c-Met receptor or induce c-Met activation was examined by measuring c-Met tyrosine phosphorylation. Phosphorylation of c-Met was measured in (1) ferret hepatocytes after 3D6 administration in vivo; and (2) a sandwich ELISA, based on the methods of Sadick et al., testing A549 cells cultured in the presence of 3D6 antibody [Sadick et al., *Anal. Biochem.*, 235:207–214 (1996)].

(1) For the ferret liver c-Met phosphorylation studies, anesthetized animals were injected with 1 ml of either rhuHGF (500 µg/ml), 3D6 (2 mg/kg), 6E10 (2 mg/kg) or 0.9% saline control into the cephalic vein. Animals were euthanised 5 minutes after injection, and the livers harvested for immunoprecipitation studies.

For immunoprecipitation, manipulations were performed at 4° C. Ferret livers were homogenized (10% w/v) in Tris-buffered saline (pH7.5), containing 10 mM CHAPS, 1 mM EGTA, 1 mM PMSF, 10 µg/ml aprotonin, 10 µg/ml leupeptin, 1 mM $Na_3VO_4$, 100 µM Na Molybdate, and 1 mM NaF. Homogenates were spun for 5 minutes at 3000 g to pellet debris. Supernatants were cleared by centrifugation at 15,000 g for 30 minutes, decanted, and then incubated for 15 minutes with protein A sepharose beads. After removal of the protein A sepharose beads by centrifugation, 1 ml of each supernatant was incubated for 2 hours with either 25 µl of agarose-coupled 4G10 beads (Upstate Biotechnology, Lake Placid, N.Y.), for tyrosine phosphorylated proteins, or with 10 µg of rabbit anti-c-Met, for total c-Met. Twenty five microliters of protein A agarose beads were added to the rabbit-anti-c-Met precipitates 90 minutes after adding the antibody. The beads were pelleted and washed 4 times in 1 ml of immunoprecipitation buffer. Beads were suspended in 50 µl of 2×Laemmli sample buffer and boiled for 5 minutes. After pelleting the beads, supernatants were decanted, 5% beta-mercaptoethanol was added and the proteins were reduced by further boiling for 5 minutes. Ten microliters of each sample were then run at 100 volts for 1 hour on a 7.5% SDS-PAGE (see FIG. 8) and transferred onto nitrocellulose membranes for 1 hour.

Transferred proteins were detected with a chemiluminescence kit (Boehringer Mannheim), following manufacturer's instructions. After blocking, the membranes were incubated for 1 hour with rabbit anti-phosphotyrosine antibody (1:2000; Zymed, South San Francisco, Calif.), and then for 1 hour with peroxidase conjugated anti-rabbit antibody (1:2000).

In vivo, tyrosine phosphorylation of c-Met in the ferret liver increased, five minutes after injection of both HGF and 3D6 (see FIG. 8). There was no change in tyrosine phosphorylation following injection with 6E10 or excipient.

(2) Microtiter plates were coated overnight at 4° C. with 5 µg/ml rabbit anti-c-Met polyclonal IgG, then non-specific binding was blocked. While the microtiter plates were coated, cultured A549 cells (human epidermoid cell line expressing c-Met; ATCC CCL 185) were washed twice with PBS and then incubated for 10 minutes at 37° C. with 3D6 or 6E10 antibodies or with rhuHGF diluted in RPMI media supplemented with 0.1% BSA, 2 mM glutamine and penicillin/streptomycin. The cells were washed twice with PBS, and then lysed in 1 ml lysis buffer (PBS, 0.2% Triton X-100, 10 µg/ml aprotonin, 5 mM NaF, 2 mM sodium orthovanadate, and 0.2 mM PMSF) for 30 minutes on an orbital shaker at room temperature. The lysate was centrifuged for 10 minutes and 100 µl supernatant was transferred in duplicate to the blocked microtiter plates. After incubation for 2 hours at 23° C., tyrosine phosphorylation was detected by incubation for 2 hours at 23° C. with biotin-anti-P-Tyr (Upstate Biotech, Lake Placid, N.Y.), followed by HRP-streptavidin. Next, TMB peroxidase substrate (KPL, Gaithersburg, Md.) was added. The reaction was stopped with phosphoric acid and OD was measured at 450 nm in an automatic plate reader. Total c-Met was measured in parallel wells incubated as above except that detection was with biotinylated rabbit anti-c-Met polyclonal IgG (NIHS biotin, Pierce Chemical).

Lysates were analyzed for relative amounts of tyrosine phosphorylated c-Met and total c-Met. As shown in FIG. 9, HGF and 3D6 induced tyrosine phosphorylation in A549 cells, without changing the total amount of c-Met.

Deposit of Materials

The following culture has been deposited with the American Type Culture Collection, (ATCC), 10801 University Boulevard, Manassas, Va. 20110-2209:

| Hybridoma | ATCC No. | Deposit Date |
|---|---|---|
| 3D6.16.1 | HB-12093 | April 30, 1996 |

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cultures deposited, since the deposited embodiments are intended as an illustration of an aspect of the invention and any cultures that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents.

What is claimed is:

1. The monoclonal antibody produced by the hybridoma cell line deposited under American Type Culture Collection Accession Number ATCC HB-12093.

2. A composition comprising a monoclonal antibody produced by the hybridoma cell line deposited under American Type Culture Collection Accession Number ATCC HB-12093 and a carrier.

3. An article of manufacture, comprising:
   a container; and
   a composition according to claim 2 contained within said container.

4. The hybridoma cell line deposited under American Type Culture Collection Accession Number ATCC HB-12093.

5. A hepatocyte growth factor (HGF) receptor agonist antibody which binds to a HGF receptor, wherein the antibody binds to the same epitope as the epitope to which the monoclonal antibody produced by the hybridoma cell line deposited under American Type Culture Collection Accession Number ATCC HB-12093 binds.

6. The antibody of claim 5 having the biological characteristics of the monoclonal antibody produced by the hybridoma cell line deposited under American Type Culture Collection Accession Number ATCC HB-12093, wherein the biological characteristics comprise inducing c-Met activation, hepatoczte proliferation and liver growth.

7. The antibody of claim 6 wherein said c-Met activation is measured by a proliferation assay measuring $^3$H-thymidine incorporation in c-Met expressing cells or in a c-Met tyrosine phosphorylation assay.

8. The antibody of claim 6, wherein the biological characteristics further comprise long serum half-life in vivo and heparin independence.

9. A composition comprising the agonist antibody of claim 5 and a carrier.

10. An article of manufacture, comprising:
    a container; and
    a composition according to claim 9 contained within said container.

11. The article of manufacture of claim 10, further comprising a label on said container.

12. The article of manufacture of claim 11, wherein the composition is effective for treating a pathological liver condition, and the label indicates that the composition can be used for treating a pathological liver condition.

13. An article of manufacture, comprising:
    a container;
    a label on said container; and
    a composition according to claim 9 contained within said container;
    wherein the composition is effective for detecting or purifying HGF receptor, and the label on said container indicates that the composition can be used for detecting or purifying HGF receptor.

14. A kit, comprising:
    (a) a first container comprising a HGF receptor agonist antibody of claim 5;
    (b) a label on said first container;
    (c) a second container comprising a pharmaceutically-acceptable buffer; and (d) instructions for using the HGF receptor agonist antibody to treat a pathological liver condition;
   wherein the agonist antibody is effective for treating a pathological liver condition, and the label on said container indicates that the agonist antibody can be used for treating a pathological liver condition.

15. The antibody of claim 5 which is a chimeric antibody.

16. The antibody of claim 5 which is a humanized antibody.

17. The antibody of claim 5 which is a human antibody.

18. The antibody of claim 5 which is an antibody fragment selected from the group consisting of Fab, Fab', F(ab')$_2$, Fv fragments, diabodies, single chain antibodies and multispecific antibodies.

19. The antibody of claim 18 which is selected from the group consisting of an Fab, Fab', F(ab')$_2$, and a single chain antibody.

20. A hybridoma cell line which produces the antibody of claim 5.

21. A method of treating a pathological liver condition in a mammal, comprising administering a hepatocyte growth effective amount of HGF receptor agonist antibody of claim 6 to the mammal.

22. The method of claim 21 wherein said pathological liver condition is selected from the group consisting of acute liver failure, alcoholic hepatitis, acute hepatitis and chronic hepatitis.

23. A method of stimulating cell proliferation, comprising exposing a cell to a HGF receptor agonist antibody of claim 5 in an amount effective to increase proliferation of the cell over that in the absence of the agonist antibody, wherein the cell is selected from the group consisting of hepatocyte, lung cell, pancreatic acinar cell, and nerve cell.

24. The method of claim 23, wherein the cell is a hepatocyte.

25. The method of claim 23, wherein the cell is a lung cell.

26. The method of claim 23, wherein the nerve cell is a Schwann cell.

27. The method of claim 23, wherein the agonist antibody is a humanized antibody.

28. The method of claim 23, wherein the agonist antibody is a chimeric antibody.

29. A method of treating a pathological liver condition in a mammal, comprising administering a heptaocyte growth effective amount of a monoclonal antibody produced by the hybridoma cell line deposited under American Type Culture Collection Accession Number ATCC HB-12093 to the mammal.

* * * * *